United States Patent
Li et al.

(10) Patent No.: US 7,674,797 B2
(45) Date of Patent: Mar. 9, 2010

(54) 2-PHENOXY- AND 2-PHENYLSULFONAMIDE DERIVATIVES WITH CCR3 ANTAGONISTIC ACTIVITY FOR THE TREATMENT OF ASTHMA AND OTHER INFLAMMATORY OR IMMUNOLOGICAL DISORDERS

(75) Inventors: Yingfu Li, Hamden, CT (US); Kevin Bacon, San Diego, CA (US); Hiromi Sugimoto, Aichi (JP); Keiko Fukushima, Saitama (JP); Kentaro Hashimoto, Wuppertal (DE); Makiko Marumo, Nara-ken (JP); Toshiya Moriwaki, Nara-ken (JP); Noriko Nunami, Hyogo-ken (JP); Naoki Tsuno, Osaka (JP); Klaus Urbahns, Lund (SE); Nagahiro Yoshida, Kyoto (JP)

(73) Assignee: Axikin Pharmaceuticals, Inc., San Diego, CA (US)

( * ) Notice: Subject to any disclaimer, the term of this patent is extended or adjusted under 35 U.S.C. 154(b) by 362 days.

(21) Appl. No.: 10/550,482

(22) PCT Filed: Mar. 11, 2004

(86) PCT No.: PCT/EP2004/002496

§ 371 (c)(1),
(2), (4) Date: Oct. 13, 2006

(87) PCT Pub. No.: WO2004/084898

PCT Pub. Date: Oct. 7, 2004

(65) Prior Publication Data

US 2007/0155725 A1    Jul. 5, 2007

(30) Foreign Application Priority Data

Mar. 24, 2003    (EP)    ................... 03006293

(51) Int. Cl.
*A01N 43/42*    (2006.01)
*A61K 31/496*    (2006.01)
*C07D 221/18*    (2006.01)
*C07D 221/22*    (2006.01)

(52) U.S. Cl. .............................. 514/279; 546/26
(58) Field of Classification Search ................. None
See application file for complete search history.

(56) References Cited

U.S. PATENT DOCUMENTS

| 2,275,354 A | 3/1942 | Ewins et al. |
| 3,819,639 A | 6/1974 | Delarge et al. |
| 2005/0070582 A1 | 3/2005 | Li et al. |

FOREIGN PATENT DOCUMENTS

| WO | WO 99/55324 A1 | 11/1999 |
| WO | WO 00/42003 A1 | 7/2000 |
| WO | WO 00/76513 A1 | 12/2000 |
| WO | WO 00/76514 A1 | 12/2000 |
| WO | WO 01/32604 A1 | 5/2001 |
| WO | WO 03/022277 A1 | 3/2003 |

OTHER PUBLICATIONS

Bertrand et al. Expert Opinion on Investigational Drugs, 2000, 9(1), 43-52.*
Ponath , P. Expert Opinion on Investigational Drugs, 1998, 7(1) 1-18.*
"NAEP's asthma bulletin board", http://www.asthma.co.za/news01.htm, accessed Aug. 5, 2008.*
Alaaeddine et al., "Production of the Chemokine RANTES by Articular Chrondrocytes and Role in Cartilage Degradation," *Arthritis & Rheumatism*, vol. 44, No. 7, pp. 1633-1643 (2001).
Ancuta et al., CD16+ monocyte-derived macrophages activate resting T cells for HIV infection by producing CCR3 and CCR4 ligands, *J. Immunol.*, vol. 176, pp. 5760-5771 (2006).
Aust et al., "Grave's disease is associated with an altered CXCR3 and CCR5 expression in thyroid-derived compared to peripheral blood lymphocytes," *Clin. Exp. Immunol.*, vol. 127, pp. 479-485 (2001).
Bhattacharya, et al., "Increased expression of eotaxin-3 distinguishes between eosinophilic esophagitis and gastroesophageal reflux disease," *Human Pathology*, vol. 38, pp. 1744-1753 (2007).
Blanchard et al., "Eotaxin-3 and a uniquely conserved gene-expression profile in eosinophilic esophagitis," *J. Clin. Invest.*, vol. 116, No. 2, pp. 536-547 (2006).
Bullock et al. "Interplay of adaptive Th2 immunity with eotaxin-3/C-C chemokine receptor 3 in eosinophilic esophagitis," *J. Pediatric Gastroenterology and Nutrition*, vol. 45, pp. 22-31 (2007).
Cheadle et al., "Eotaxin-2 and colorectal cancer: a potential target for immune therapy," *Human Cancer Biol.*, vol. 13, No. 19, pp. 5719-5728 (2007).
CHEMCATS Database, Ambinter Stock Screening Collection, Order Nos. 7J-012, 7J-005 and 7J-004.
Chi et al., "C-Reactive protein enhances expression of chemokine receptors on mast cells," *The FASEB Journal*, vol. 16, No. 4, p. A690, abstract 514.2.
Delarge, J., "Nouveaux Anti-inflammatoires Derives de la Pyridine," *Ann. Pharm. Fr.*, 1973, vol. 31, No. 6, pp. 467-474. (English summary at p. 474).

(Continued)

*Primary Examiner*—James O Wilson
*Assistant Examiner*—Noble Jarrell
(74) *Attorney, Agent, or Firm*—Jones Day

(57) ABSTRACT

The present invention relates to a benzenesulfonamide derivative of formula (I), which is useful as an active ingredient of pharmaceutical preparations. The benzenesulfonamide derivatives of the present invention have CCR3 (CC type chemokine receptor) antagonistic activity, and can be used for the prophylaxis and treatment of diseases associated with CCR3 activity, in particular for the treatment of asthma, atopic dermatitis, allergic rhinitis and other inflammatory/immunological disorders. In said formula, X represents O or S; $R^4$ represents formulae (a), (b), (c), (d), (e), (f), (g), (h), (i) or (j), the other substituents are as defined in claim 1.

10 Claims, No Drawings

OTHER PUBLICATIONS

Dol et al., "Angiotensin AT1 receptor antagonist irbesartan decreases lesion size, chemokine expression, and macrophage accumulation in apolipoprotein E-deficient mice," *J. Cardiovascular Pharmacology*, vol. 38, pp. 395-405 (2001).
Elsner et al., "Human Eotaxin Represents a Potential Activator of the Respiratory Burst of Human Eosinophils," Eur. J. Immunol., vol. 26, pp. 1919-1925 (1996).
Foster et al., "Elemental signals regulating eosinophil accumulation in the lung," *Immunol. Rev.*, vol. 179, pp. 173-181 (2001).
Gerber et al., "Functional expression of the eotaxin receptor CCR3 in T lymphocytes co-localizing with eosinophils," *Current Biology*, vol. 7, pp. 836-843 (1997).
Haley et al., "Overexpression of Eotaxin and the CCR3 Receptor in Human Atherosclerosis: Using Genomic Technology to Idenify a Potential Novel Pathway of Vascular Inflammation," *Circulation*, vol. 102, pp. 2185-2189 (2000).
Hogaboam et al., "Collagen Deposition in Non-Fibrotic Lung Granuloma Model after Nitric Oxide Inhibition," *Am. J. Pathology*, vol. 153, No. 6, pp. 1861-1872 (1998).
Hsu et al., "Production of the chemokine eotaxin-1 in osteoarthritis and its role in cartilage degradation," *J. Cellular Biochem.*, vol. 93, pp. 929-939 (2004).
Huaux et al., "Role of eotaxin-1 (CCL11) and CC chemokine receptor 3 (CCR3) in bleomycin-induced lung injury and fibrosis," vol. 167, No. 6, pp. 1485-1496 (2005).
Hunt et al., "Newly identified genetic risk variants for celiac disease related to the immune response," *Nature Genetics*, vol. 40, No. 4, pp. 395-402 (2008).
International Search Report of International Application No. PCT/EP2002/09873 having a Publication No. WO 2003/022277.
International Search Report of International Application No. PCT/EP2004/002496 having a Publication No. WO 2004/084898.
Jahnz-Royk et al., "Eotaxin in serum of patients with asthma or chronic obstructive pulmonary disease: relationship with eosophil cationic protein and lung function," *Mediators of Inflam.*, vol. 9, pp. 175-179 (2000).
Johrer et al., "Up-regulation of functional chemokine receptor CCR3 in human renal cell carcinoma," *Human Cancer Biol.*, vol. 11, No. 7, pp. 2459-2465 (2005).
Joubert et al., "CCR3 expression and function in asthmatic airway smooth muscle cells," *J. Immunol.*, vol. 175, pp. 2702-2708 (2005).
Katschke et al., "Differential Expression of Chemokine Receptors on Peripheral Blood, Synovial Fluid, and Synovial Tissue Monocytes/Macrophages in Rheumatoid Arthritis," *Arthritis & Rheumatism*, vol. 44, No. 5, pp. 1022-1032 (2001).
Kouno et al. "Up-regulation of CC chemokine, CCL3L1, and receptors, CCR3, CCR5 in human glioblastoma that promotes cell growth," *J. Neuro-Oncology*, vol. 70, pp. 301-307 (2004).
Lamkhioued et al., "Increased expression of eotaxin in bronchoaveolar lavage and airways of asthmatics contributes to the chemotaxis of eosinophils to the site of inflammation," *J. Immunol.*, vol. 159, pp. 4593-4601 (1997).
Li et al., "Mast Cells/Basophils in the Peripheral Blood of Allergic Individuals Who Are HIV-1 Susceptible Due to Their Surface Expression of CD4 and the Chemokine Receptors CCR3, CCR5 and CXCR4," *Blood*, vol. 97, No. 11, pp. 3484-3487 (2001).
Marone et al., "Human mast cells and basophils in HIV-1 Infection," *Trends Immunol.*, vol. 22, No. 5., pp. 229-232 (2001).
Marone et al., "Are Mast Cells MASTers in HIV-1 Infection?," *Int. Arch. Allergy Immunol.*, vol. 125, pp. 89-95 (2001).
Mastrukova et al., "The Application of the Hammett Equation to the Theory of Tautomeric Equilibrium-II," *Tetrahedron*, 1963, vol. 19, pp. 357-372.
Matsukura et al., "Expression of RANTES by normal airway epithelial cells after influenza virus A infection," *Am. J. Respir. Cell and Mol. Biol.*, vol. 18, pp. 255-264 (1998).
Nissinen et al., "CCR3, CCR5 interleukin 4, and interferon-gamma expression on synovial and peripheral T cells and monocytes in rheumatoid arthritis," *J. Rheumatol.*, vol. 30, No. 9, pp. 1928-1934 (2003).
Ohagen et al., "Genetic and functional analysis of full-length human immunodeficiency virus type 1 env genes derived from brain and blood or patients with AIDS," *J. Virology*, vol. 77, No. 22, pp. 12336-12345 (2003).
Oliviera et al., "Stem cell factor and IgE-stimulated murine mast cells produce chemokines (CCL2, CCL17, CCL22) and express chemokine receptors," *Inflamm. Res.*, vol. 50, pp. 168-174 (2001).

Park et al., "CD4 Receptor-Dependent Entry of Human Immunodeficiency Virus Type-1 env-Pseudotypes into CCR5-, CCR3- and CXCR4-Expressing Human Alveolar Macrophages Is Preferrentially Mediated by the CCR5 Coreceptor," *Am. J. Respir. Cell Mol. Biol.*, vol. 20, pp. 864-871 (1999).
Rothenberg et al., "Targeted Disruption of the Chemokine Eotaxin Partially Reduces Antigen-induced Tissue Eosophilia," *J. Exp. Med.*, vol. 185, pp. 785-790 (1997).
Ruth et al., "Expression and Participation of Eotaxin During Mycobacterial (Type 1) and Schistosomal (Type 2) Antigen-Elicited Granuloma Formation," *J. Immunology*, vol. 161, No. 8, pp. 4276-4282 (1998).
Saari et al., "Synthesis and Evaluation of Some Nitrobenzenesulfonamides Containing Nitroisopropyl and (Ureidooxy)methyl Groups as Novel Hypoxic Cell Selective Cytotoxic Agents," *J. Med. Chem.* 1991, 34, 3132-3138.
Sabroe et al., *J. Immunol.*, "Cloning and Characterization of the Guinea Pig Eosinophil Eotaxin Receptor, C-C Chemokine Receptor-3: Blockade Using a Monoclonal Antibody In Vivo," vol. 161, pp. 6139-6147 (1998).
Sallusto et al., "Selective Expression of the Eotaxin Receptor CCR3 by Human T Helper 2 Cells," *Science*, vol. 277, pp. 2005-2007 (1997).
Saito et al., "Selective regulation of chemokine production in human epithelial cells," *J. Infect. Dis.*, vol. 175, pp. 479-504 (1997).
Silva et al., "Differential expression of chemokines and chemokine receptors in inflammatory periapical diseases," *Oral Microbiol. Immunol.*, vol. 20, pp. 310-316 (2005).
Simchen et al. "Expression and Regulation of Regulated on Activation, Normal T Cells Expressed and Secreted in Thyroid Tissue of Patients with Graves' Disease and Thyroid Autonomy and in Thyroid-Derived Cell Populations," *J. Clinical Endocrinology & Metabolism*, vol. 85, No. 2, 4758-4764 (2000).
Stellato et al., "Cutting Edge: Expression of the C-C Chemokine Receptor CCR3 in Human Airway Epithelial Cells," *J. Immunology*, 1457-1460 (2001).
Sugasawa et al., "Prognostic significance of expression of CCL5/RANTES receptors in patients with gastric cancer," *J. Sergical Oncology*, vol. 97, pp. 445-450 (2008).
Teixeira et al., "Increased serum levels of CCL11/eotaxin in schizophrenia," *Progress in Neuro-pharmacology & Biol. Psych.*, vol. 32, pp. 710-714 (2008).
Uguccioni et al., "High Expression of the Chemokine Receptor CCR3 in Human Blood Basophils," *J. Clin. Invest.*, vol. 100, pp. 1137-1143 (1997).
Weeraratna et al., "Alterations in immunological and neurological gene expression patterns in Alzheimer's disease tissues," *Exp. Cell. Res.*, vol. 313, pp. 450-461 (2007).
White et al., "Identification of potent, selective, non-peptide CC chemokine receptor-3 antagonist that inhibits eotaxin-, eotaxin-2-, and monocyte chemotactic protein-4-induced eosinophil migration," *J. Bio. Chem.*, vol. 275, No. 47, pp. 36626-36631 (2000).
Xia et al., "Immunihistochemical Study of the β-Chemokine Receptors of CCR3 and CCR5 and Their Ligands in Normal and Alzheimer's Diseases Brains," *Am. J. Pathology*, vol. 153, No. 1, pp. 31-36 (1998).
Xia et al., "Chemokines/Chemokine Receptors in the Central Nervous System and Alzheimer's Disease," *J. Neurovirology*, vol. 5, pp. 32-41 (1999).
Xia et al., "Expression of the chemokine receptor CXCR3 on neurons and the elevated expression of its ligand IP-10 in reactive astrocytes: in vitro ERK 1/2 activation and role in Alzheimer's disease," *J. Immunol.*, 108, 227-235 (2000).
Ying et al., "Enchanced expression of eotaxin and CCR3 mRNA and protein in atopic asthma. Association with airway hyperresponsiveness and predominant colocalization of eotaxin mRNA to bronchial epithelial and endothelial cells," *Eur. J. Immunol.* vol. 27, 3507-3516 (1997).
Corren, J., "Allergic rhinitis and asthma: How important is the link?," *J. Allergy Clin. Immunol.*, vol. 99, pp. S781-S786 (1997).
Terada et al., "Biochemical properties of eosinophils and their preferential accumulation mechanism in nasal allergy," *J. Allergy Clin. Immunol.*, vol. 94, pp. 629-642 (1994).
"Chemokine CCR3 Antagonists," *Exp. Opin. Ther. Patents*, 2000, 10(9): 1455-1459.

\* cited by examiner

2-PHENOXY- AND 2-PHENYLSULFONAMIDE DERIVATIVES WITH CCR3 ANTAGONISTIC ACTIVITY FOR THE TREATMENT OF ASTHMA AND OTHER INFLAMMATORY OR IMMUNOLOGICAL DISORDERS

This application is the U.S. National Stage of International Patent Application No. PCT/EP2004/002496, filed Mar. 11, 2004, which claims priority to European Patent Application No. 03006293.9, filed Mar. 24, 2003, all of which are incorporated herein by reference in their entirety.

TECHNICAL FIELD

The present invention relates to a benzenesulfonamide derivative, which is useful as an active ingredient of pharmaceutical preparations. The benzenesulfonamide derivatives of the present invention have CCR3 (CC type chemokine receptor 3) antagonistic activity, and can be used for the prophylaxis and treatment of diseases associated with CCR3 activity, in particular for the treatment of asthma, atopic dermatitis, allergic rhinitis and other inflammatory/immunological disorders.

BACKGROUND ART

Chemokines are chemotactic cytokines of which major functions are migration of inflammatory cells that express relevant chemokine receptors on their surfaces to sites of inflammation, and activation of inflammatory cells. There are two classes of chemokines, C-X-C (.alpha.) and C-C (i), depending on whether the first two cysteines are separated by a single amino acid (C-X-C) or are adjacent (C-C).

Eotaxin, one of the C-C family of chemokines, is an 8.4 kDa (74 amino acid) polypeptide and binds solely to the receptor CCR3 with high affinity. In vitro and in vivo, eotaxin causes chemotaxis of inflammatory cells expressing CCR3 [Elsner J., Hochstetter R., Kimming D. and Kapp A.: Human eotaxin represents a potent activator of the respiratory burst of human eosinophils. Eur. J. Immunol., 26: 1919-1925, 1996].

The chemokine receptor CCR3 is a G protein-coupled, seven transmembrane domain receptor (GPCR) which binds to known ligands, in addition to eotaxin, including eotaxin-2 (CCL24), RANTES (CCL5), MCP-3 (CCL7) and MCP-4 (CCL13). CCR3 is expressed on inflammatory cells relevant to the chronic asthma pathology. Such inflammatory cells include Eosinophils [Sabroe I., Conroy D. M., Gerard N. P., Li Y., Collins P. D., Post T. W., Jose P. J., Williams T. J., Gerard C. J., Ponath P. D. J. Immunol. 161: 6139-6147, 1998], basophils [Uguccioni M., Mackay C. R., Ochensberger B., Loetscher P., Rhis S., LaRosa G. J., Rao P., Ponath P. D., Baggiolini M., Dahinden C. A. J. Clin. Invest. 100: 1137-1143, 1997], Th2 cells [Sallusto F., Mackay C. R., Lanzavecchia A. Science. 277: 2005-2007, 1997], alveolar macrophages [Park I. W., Koziel H., Hatch W., Li X., Du B., Groopman J. E. Am. J. Respir. Cell Mol. Biol. 20:864-71, 1999] and mast cells [Oliveira S. H. and Lukacs N. W. Inflamm. Res. 50: 168-174. 2001]. It was also reported that BEAS-2B, an epithelial cell line, stimulated with TNF-α and IFN-γ, expressed CCR3 [Stellato C., Brummet M. E., Plitt J. R., Shahabuddin S., Baroody F. M., Liu M., Ponath P. D., and Beck L. A. J. Immunol., 166: 1457-1461, 2001].

In animal models, eotaxin-knockout mice showed decreased eosinophilia after antigen challenge [Rothenberg M. E., MacLean J. A., Pearlman E., Luster A. D. and Leder P. J. Exp. Med., 185: 785-790, 1997]. In IL5-/eotaxin-double knock-out mice, there is no eosinophilia or AHR in response to antigen challenge [Foster P. S., Mould A. W., Yang M., Mackenzie J., Mattes J., Hogan S. P., Mahalingam S., Mckenzie A. N. J., Rothenberg M. E., Young I. G., Matthaei K. I. and Webb D. C. Immunol. Rev., 179, 173-181, 2001]. Clinically, mRNA and protein expression of eotaxin and CCR3 are observed in the lung tissues of atopic asthmatics and are associated with AHR, reduced $FEV_1$ and lung eosinophilia [Ying S., Robin D. S., Meng Q., Rottman J., Kennedy R., Ringler D. J., Mackay C. R., Daugherty B. L., Springer M. S., Durham S. R., Williams T. J. and Kay A. B.: Enhanced expression of eotaxin and CCR3 mRNA and protein in atopic asthma. Association with airway hyperresponsiveness and predominant colocalization of eotaxin mRNA to bronchial epithelial and endothelial cells. Eur. J. Immunol., 27, 3507-3516, 1997; Lamkhioued Renzi P. M., AbiYounes S., GarciaZepada E. A., Allakhverdi Z., Ghaffar O., Rothenberg M. D., Luster A. D. and Hamid Q.: Increased expressions of eotaxin in bronchoalveolar lavage and airways of asthmatics contributes to the chemotaxis of eosinophils to the site of inflammation. J. Immunol., 159: 4593-4601, 1997; Jahnz-Royk K., Plusa T. and Mierzejewska J.: Eotaxin in serum of patients with asthma or chronic obstructive pulmonary disease: relationship with eosinophil cationic protein and lung function. Mediators of Inflammation, 9: 175-179, 2000]. In addition, in allergic rhinitis, CCR3-expressing Th2 lymphocytes co-localize with eosinophils in nasal polyps in close proximity to eotaxin-expressing cells [Gerber B. O., Zanni M. P., Uguccioni M., Loetscher M., Mackay C. R., Pichler W. J., Yawalkar N., Baggiolini M. and Moser B.: Functional expression of the eotaxin receptor CCR3 in T lymphocytes co-localizing with eosinophils. CURRENT BIOLOGY 7: 836-843, 1997]. Moreover, viral infections (RSV, influenza virus) which are known risk factors in asthma, result in increased eotaxin expression in lung tissue which is correlated with tissue eosinophilia [Matsukura S., Kokubo F., Kubo H., Tomita T., Tokunaga H., Kadokura M., Yamamoto T., Kuroiwa Y., Ohno T., Suzaki H. and Adachi M.: Expression of RANTES by normal airway epithelial cells after influenza virus A infection. Am. J. Respir. Cell and Mol. Biol., 18: 255-264, 1998; Saito T., Deskin R. W., Casola A., Haeberle H., Olszewska B., Ernest P. B., Alam R., Ogra P. L. and Garofalo R.: Selective regulation of chemolcine production in human epithelial cells. J. Infec. Dis., 175: 497-504, 1997]. Thus the binding of CCR3 and related chemokine including eotaxin has been implicated as being important mediators of inflammatory and immunoregulatory disorders and diseases, including asthma, rhinitis, and allergic diseases, as well as autoimmune pathologies such as rheumatoid arthritis, Grave's disease, and atherosclerosis.

It is also implicated that binding of CCR3 and related chemokine is an important factor of virus infections including HIV [(Marone G, de Paulis A, Florio G, Petraroli A, Rossi F, Triggiani M.: Int Arch Allergy Immunol 2001 June; 125(2)/89-95), (Li Y et al.,: Blood 2001 Jun. 1; 97(11):3484-90), and (Marone G, Florio G, Petraroli A, Triggiani M, de Paulis A: Trends Immunol 2001 May; 22 (5):229-32)], lung granuloma (Ruth J H, Lukacs N W, Warmington K S, Polak T J, Burdick M, Kunkel S L, Strieter R M, Chensue S W: J Immunol 1998 Oct. 15; 161 (8):4276-82), and Alzheimer's diseases (Xia M Q, Qin S X, Wu L J, Mackay C R, and Hyman B T: Am J Pathol 1998 July; 153 (1):31-37).

Therefore, CCR3 is an important target and antagonism of CCR3 is likely to be effective in the treatment of such inflammatory and immunoregulatory disorders, and diseases.

WO 2000/76514 and WO 2000/76513 disclose cyclopentyl modulators of chemokine receptors including CCR3 activity represented by the general formula:

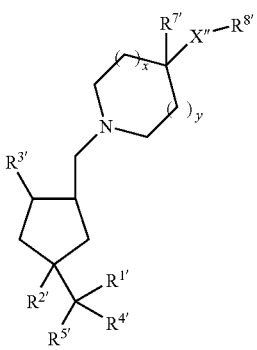

wherein

X", x, y, R$^{1'}$, R$^{2'}$, R$^{3'}$, R$^{4'}$ R$^{5'}$, R$^{6'}$ R$^{7'}$ and R$^{8'}$ are defined in the application.

Other applications also disclose CCR$^3$ modulators. However, none of the reference and other reference discloses simple benzenesulfonamide derivatives having CCR$^3$ antagonistic activity.

The development of a compound having effective CCR3 antagonistic activity can be used for the prophylaxis and treatment of diseases associated with CCR3 activity has been desired.

SUMMARY OF THE INVENTION

As the result of extensive studies on chemical modification of benzenesulfonamide derivatives, the present inventors have found that the compounds of the structure related to the present invention have unexpectedly excellent CCR3 antagonistic activity. The present invention has been accomplished based on these findings.

This invention is to provide novel benzenesulfonamide derivatives shown by the following formula (I), its tautomeric and stereoisomeric form, and the salts thereof.

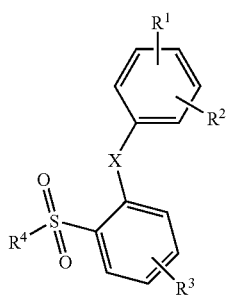

(I)

wherein

X represents O or S;

R$^1$ represents hydrogen, halogen, hydroxy, nitro, cyano, C$_{1-6}$ alkoxy carbonyl, amino, C$_{1-6}$ alkylamino, di(C$_{1-6}$ alkyl)amino, C$_{1-6}$ alkanoyl, phenyl, C$_{1-6}$ alkyl optionally substituted by mono-, di- or tri-halogen, or C$_{1-6}$ alkoxy optionally substituted by mono-, di- or tri-halogen;

R$^2$ represents hydrogen, halogen, hydroxy, nitro, cyano, C$_{1-6}$ alkoxy carbonyl, amino, C$_{1-6}$ alkylamino, di(C$_{1-6}$ alkyl) amino, C$_{1-6}$ alkanoyl, phenyl, C$_{1-6}$ alkyl optionally substituted by mono-, di- or tri-halogen or C$_{1-6}$ alkoxy optionally substituted by mono-, di- or tri-halogen;

R$^3$ represents hydrogen, halogen, hydroxy, nitro, cyano, amino, carboxy, tetrazolyl, C$_{1-6}$ alkoxy, C$_{1-6}$ alkoxycarbonyl, C$_{1-6}$ alkanoyl, C$_{1-6}$ alkanoylamino, C$_{1-6}$ alkyl optionally substituted by mono-, di- or tri-halogen or hydroxy;

R$^4$ represents

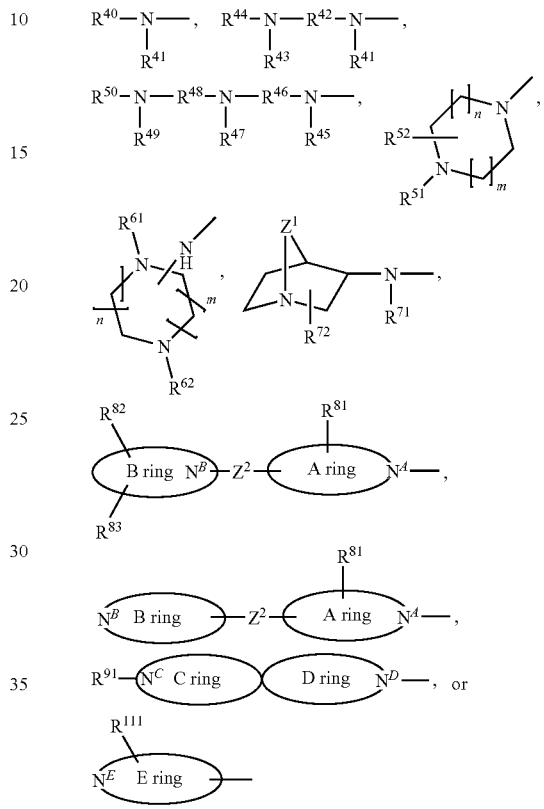

wherein

R$^{40}$ represents C$_{1-6}$ alkyl substituted by pyrrolidinyl or piperidinyl wherein said pyrrolidinyl and piperidinyl are optionally substituted by mono- or di-oxo, 7-oxa-bicyclo[4.1.0]hept-3-yl optionally having 1 or 2 substituents selected from the group consisting of amino, (C$_{1-6}$ alkyl)amino and di(C$_{1-6}$ alkyl)amino, or a 5 to 8 membered saturated heterocyclic ring containing 1 or 2 heteroatoms selected from the group consisting of N and O and optionally having from 1 to 3 substituents selected from the group consisting of hydroxy, amino, oxo and C$_{1-6}$ alkyl;

R$^{41}$ represents hydrogen, C$_{1-6}$ alkyl optionally substituted by amino, C$_{1-6}$ alkylamino, di(C$_{1-6}$ alkyl)amino, or 2,5-dioxopyrrolidin-1-yl or a C$_{5-8}$ cycloalkyl optionally substituted by hydroxy, or R$^{40}$ and R$^{41}$ may form, together with adjacent N atom, a 5 to 8 membered saturated heterocyclic ring optionally interrupted by O;

R$^{42}$ represents C$_{1-6}$ alkylene optionally substituted by hydroxy or carboxy, or a C$_{5-8}$ cycloalkyl substituted by at least one hydroxy and moreover optionally 1 or 2 substituents selected from the group consisting of hydroxy, amino, oxo and C$_{1-6}$ alkyl, or R$^{41}$ and R$^{42}$ may form, together with adjacent N atom, a 5 to 8 membered saturated heterocyclic ring optionally interrupted by NH or O, wherein said 5 to 8 membered saturated heterocyclic ring is substituted by mono- or di-oxo, with the proviso that when $R^{41}$ is hydrogen, $C_{1-6}$ alkyl optionally substituted by amino, $C_{1-6}$ alkylamino, or di($C_{1-6}$ alkyl)amino, $R^{42}$ is hydroxy substituted $C_{1-6}$ alkylene or carboxy substituted $C_{1-6}$ alkylene;

$R^{43}$ represents hydrogen, or $C_{1-6}$ alkyl optionally substituted by hydroxy or carboxy;

$R^{44}$ represents hydrogen, or $C_{1-6}$ alkyl optionally substituted by hydroxy or carboxy, with the proviso that when $R^{41}$ and $R^{42}$ form, together with adjacent N atom, a 5 to 8 membered saturated heterocyclic ring, $R^{44}$ represents hydroxy substituted $C_{1-6}$ alkyl or carboxy substituted $C_{1-6}$ alkyl;

$R^{45}$, $R^{47}$, $R^{49}$ and $R^{50}$ independently represent hydrogen or $C_{1-6}$ alkyl;

$R^{46}$ and $R^{48}$ independently represent $C_{1-6}$ alkylene optionally substituted hydroxy or carboxy;

n represents an integer selected from 1 to 3;

m represents an integer selected from 0 to 3;

$R^{51}$ represents hydrogen, $C_{1-6}$ alkyl, or a 3 to 8 membered saturated ring optionally interrupted by NH or O;

$R^{52}$ represents hydrogen, $C_{1-6}$ alkoxy carbonyl, or $C_{1-6}$ alkyl substituted by carboxy, amino, ($C_{1-6}$ alkyl)amino, di($C_{1-6}$ alkyl)amino, N—($C_{1-6}$ alkylsulfonyl)amino, N—($C_{1-6}$ alkanoyl)amino, $C_{1-6}$ alkoxycarbonyl, tetrazolyl, triazolyl, indolinyl, isoindolinyl, indolyl, isoindolyl, pyrrolidinyl optionally substituted by mono- or di-oxo, or piperidinyl optionally substituted by mono- or di-oxo, with the proviso that when $R^{51}$ and $R^{52}$ are hydrogen at the same time, $R^3$ is tetrazolyl or $C_{1-6}$ alkanoyl, or when $R^{51}$ is hydrogen or $C_{1-6}$ (alkyl, $R^{52}$ is other than hydrogen;

$R^{61}$ and $R^{62}$ independently represent hydrogen or C, (alkyl optionally substituted by hydroxy, carboxy, phenyl or mono-, di- or tri halogen;

$R^{71}$ represents hydrogen, or $C_{6-4}$ alkyl optionally substituted by amino, hydroxy, carboxy, pyrrolidinyl or piperidinyl, wherein said pyrrolidinyl and piperidinyl are optionally substituted by mono- or di-oxo;

$R^{72}$ represents hydrogen, carboxy, $C_{1-6}$ alkanoyl, amino, ($C_{1-6}$alkyl)amino, di-($C_{1-6}$alkyl)amino, N—($C_{1-6}$alkyl) amino carbonyl, $C_{1-6}$ alkyl optionally substituted by hydroxy, carboxy, or mono-, di- or tri-halogen, $C_{1-6}$ alkoxy optionally substituted by mono-, di- or tri-halogen, pyrrolidinyl or piperidinyl, wherein said pyrrolidinyl and piperidinyl are optionally substituted by mono- or di-oxo;

$Z^1$ represents —$[CH_2]_p$—, wherein p represents an integer 1 or 2;

$R^{81}$ represents hydrogen, $C_{1-6}$ alkoxycarbonyl, or $C_{1-6}$ alkyl substituted by pyrrolidinyl, or piperidinyl, wherein said pyrrolidinyl and piperidinyl are optionally substituted by mono- or di-oxo;

$R^{82}$ represents hydrogen, hydroxy, carboxy or $C_{1-6}$ alkyl substituted by hydroxy, amino, or carboxy, $R^{83}$ represents hydrogen, hydroxy, carboxy, or $C_{1-6}$ alkyl substituted by hydroxy, amino, or carboxy, with the proviso that when $R^{81}$ is hydrogen, $R^{82}$ or $R^{83}$ is other than hydrogen;

$Z^2$ represents —$[CH_2]_q$—, wherein q represents an integer selected from 0 to 3;

$R^{91}$ represents hydrogen or $C_{1-6}$ alkyl optionally substituted by phenyl;

$R^{111}$ represents hydrogen, carboxy, $C_{1-6}$ alkoxy carbonyl, $C_{1-6}$ alkanoyl, N—($C_{1-6}$alkyl) aminocarbonyl, $C_{1-6}$ alkoxy optionally substituted by mono-, di- or tri-halogen, or $C_{1-6}$ alkyl optionally substituted by hydroxy, mono-, di- or tri-halogen, amino, ($C_{1-6}$ alkyl)amino, di($C_{1-6}$ alkyl)amino, N—($C_{1-6}$ alkylsulfonyl)amino, N—($C_{1-6}$ alkanoyl)amino, $C_{1-6}$ alkoxycarbonyl, tetrazolyl, triazolyl, indolinyl, isoindolinyl, indolyl, isoindolyl, pyrrolidinyl or piperidinyl wherein said pyrrolidinyl and piperidinyl are optionally substituted by mono- or di-oxo;

A ring represents a 3 to 8 membered saturated heterocyclic ring, in which the nitrogen atom $N^A$ is the only hetero atom;

B ring represents a 3 to 8 membered saturated heterocyclic ring, in which the nitrogen atom $N^B$ is the only hetero atom;

C ring and D ring together form a 7 to 15 membered diazabicyclic ring; and

E ring represents a 5 to 8 membered saturated heterocyclic ring, in which the nitrogen atom $N^E$ is the only hetero atom.

This invention is also to provide a method for treating or preventing a CCR3 related disorder or disease in a human or animal subject, comprising administering to said subject a therapeutically effective amount of the benzenesulfonamide derivative shown in the formula (I), its tautomeric or stereoisomeric form, or a physiologically acceptable salt thereof.

Further this invention is to provide a use of the benzenesulfonamide derivative shown in the formula (I), its tautomeric or stereoisomeric form, or a physiologically acceptable salt thereof in the preparation of a medicament for treating or preventing a CCR3 related disorder or disease.

The compounds of the present invention surprisingly show excellent CCR3 antagonistic activity. They are, therefore suitable for the production of medicament or medical composition, which may be useful to treat CCR3 related diseases. More specifically, since the compounds of the present invention antagonize CCR3, they are useful for treatment and prophylaxis of diseases as follows; asthma, rhinitis, and allergic diseases, and autoimmune pathologies such as rheumatoid arthritis, Grave's disease, and atherosclerosis. Therefore, CCR3 is an important target and antagonism of CCR3 is likely to be effective in the treatment and prophylaxis of such inflammatory and immunoregulatory disorders and diseases.

The compounds of the present invention are also useful for treatment and prophylaxis of diseases like virus infections including HIV, lung granuloma, and Alzheimer's diseases, since the diseases also relate to CCR3.

In another embodiment, the compounds of formula (I) are those wherein:

$R^4$ represents

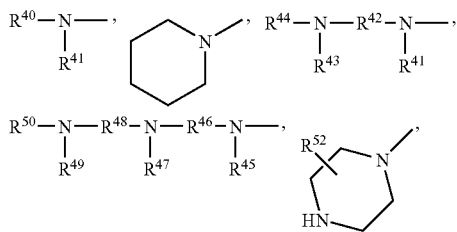

-continued

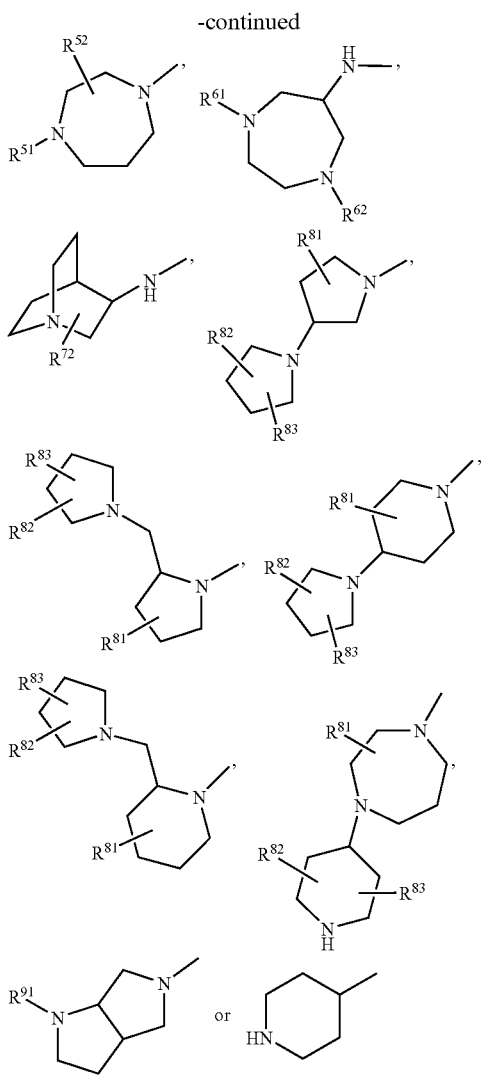

wherein

R⁴⁰ represents $C_{1-6}$ alkyl having substituent selected from the group consisting of 2-oxo pyrrolidin-1-yl, 2,5-dioxo pyrrolidin-1-yl, 2-oxo-piperidin-1-yl, 2-oxo-piperidin-3-yl, 4-oxo-piperidin-1-yl, 2-oxo-piperidin-6-yl, 2,5-dioxo-piperidin-1-yl, 2,6-dioxo-piperidin-1-yl, and 2,6-dioxo-piperidin-3-yl, piperidin-1-yl, -2-yl, -3-yl or 4-yl (wherein said piperidin is optionally substituted by mono- or di-oxo), hexahydroazepin-1-yl,-2-yl, -3-yl or -4-yl (wherein said hexahydroazepin is optionally substituted by mono- or di-oxo), and 7-oxa-bicyclo[4.1.0]hept-3-yl optionally substituted by amino;

R⁴¹ represents hydrogen, cyclopentyl or $C_{1-6}$ alkyl optionally substituted by amino, $C_{1-6}$ alkyl amino, di-($C_{1-6}$ alkyl)amino, or 2,5-dioxo pyrrolidin-1-yl, R⁴² represents $C_{1-6}$ alkylene substituted by carboxy or cyclohexyl substituted by mono- or di-hydroxy, R⁴¹ and R⁴² may form, together with adjacent N atom, a 5 or 6 membered saturated heterocyclic ring;

with the proviso that when R⁴¹ is hydrogen, $C_{1-6}$ alkyl optionally substituted by amino, $C_{1-6}$ alkylamino, or di($C_{1-6}$ alkyl)amino, R⁴² is hydroxy substituted $C_{1-6}$ alkylene or carboxy substituted $C_{1-6}$ alkylene;

R⁴³ represents hydrogen or $C_{1-6}$ alkyl optionally substituted by hydroxy,

R⁴⁴ represents $C_{1-6}$ alkyl optionally substituted by hydroxy or carboxy,

With the proviso that when R⁴¹ and R⁴² form, together with adjacent N atom, a 5 or 6 membered saturated heterocyclic ring, R⁴⁴ is hydroxy substituted $C_{1-6}$ alkyl or carboxy substituted $C_{1-6}$ alkyl;

R⁴⁵, R⁴⁷, R⁴⁹ and R⁵⁰ independently represent hydrogen, methyl or ethyl;

R⁴⁶ and R⁴⁸ independently represent $C_{1-6}$ alkylene optionally substituted hydroxy or carboxy;

R⁵¹ represents hydrogen, cyclopentyl, ethyl or methyl;

R⁵² represents methoxycarbonyl or $C_{1-6}$ alkyl substituted by carboxy, amino, methoxy-carbonyl, methanesulfonylamino, acetamido, indolyl, tetrazolyl, 1,2,3-triazolyl, 1,2,4-triazolyl, 1,2,5-triazolyl, 1,3,4-triazolyl, pyrrolidin-1-yl, 2-oxo-pyrrolidin-1-yl, 2,5-dioxo pyrrolidin-1-yl, 2-oxo-piperidin-1-yl, 2-oxo-piperidin-3-yl, 4-oxo-piperidin-1-yl, 2-oxo-piperidin-6-yl, 2,5-dioxo-piperidin-1-yl, 2,6-dioxo-piperidin-1-yl, or 2,6-dioxo-piperidin-3-yl;

R⁶¹ and R⁶² independently represent benzyl or phenethyl;

R⁷² represents hydrogen, carboxy, $C_{1-6}$ alkanoyl, amino, ($C_{1-6}$alkyl)amino, di-($C_{1-6}$-alkyl)amino, N—($C_{1-6}$alkyl)amino carbonyl, $C_{1-6}$ alkyl optionally substituted by hydroxy, carboxy, or mono-, di- or tri-halogen, $C_{1-6}$ alkoxy optionally substituted by mono-, di- or tri-halogen, pyrrolidinyl or piperidinyl wherein said pyrrolidinyl and piperidinyl are optionally substituted by mono- or di-oxo;

R⁸¹ represents hydrogen, methoxycarbonyl or $C_{1-6}$ alkyl substituted by 2-oxo-pyrrolidin-1-yl, 2,5-dioxo pyrrolidin-1-yl, 2-oxo-piperidin-1-yl, 2-oxo-piperidin-3-yl, 4-oxo-piperidin-1-yl, 2-oxo-piperidin-6-yl, 2,5-dioxo-piperidin-1-yl, 2,6-dioxo-piperidin-1-yl, or 2,6-dioxo-piperidin-3-yl;

R⁸² represents hydrogen, hydroxy or $C_{1-6}$ alkyl substituted by hydroxy;

R⁸³ represents hydrogen, hydroxy or carboxy;

with the proviso that when R⁸² and R⁸³ are hydrogen at the same time, R⁸¹ is other than hydrogen, or when R⁸¹ and R⁸³ are hydrogen at the same time, R⁸² is other than hydrogen;

R⁹¹ represents benzyl or phenethyl.

Yet other preferred compounds of formula (I) represent formula (I-b) and are those

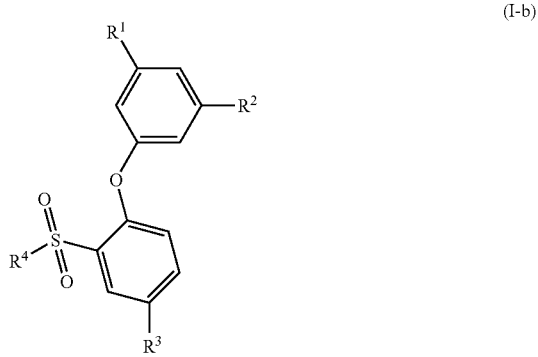

(I-b)

wherein
R¹ represents fluoro, chloro, bromo, iodo, or nitro;

$R^2$ represents fluoro, chloro, bromo, iodo, or nitro;
$R^3$ represents acetyl, cyano, or tetrazolyl;
$R^4$ represents

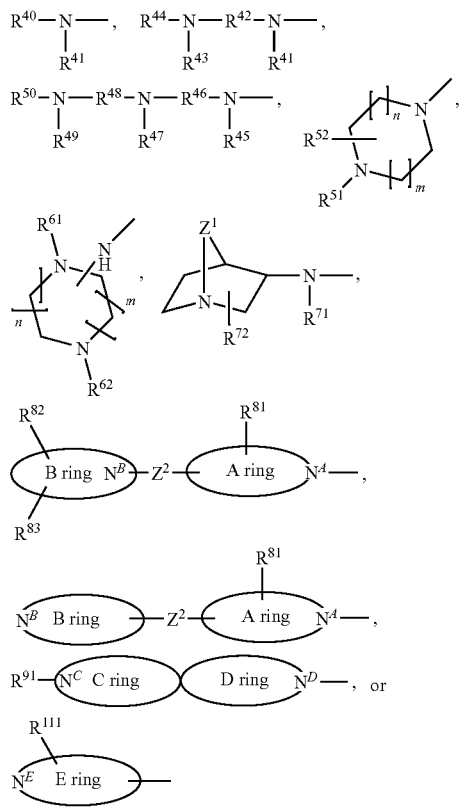

wherein
$R^{40}$ represents $C_{1-6}$ alkyl substituted by pyrrolidinyl or piperidinyl wherein said pyrrolidinyl and piperidinyl are optionally substituted by mono- or di-oxo, 7-oxa-bicyclo[4.1.0]hept-3-yl optionally having 1 or 2 substituents selected from the group consisting of amino, ($C_{1-6}$ alkyl)amino and di($C_{1-6}$ alkyl)amino, or a 5 to 8 membered saturated heterocyclic ring containing 1 or 2 heteroatoms selected from the group consisting of N and O and optionally having from 1 to 3 substituents selected from the group consisting of hydroxy, amino, oxo and $C_{1-6}$ alkyl;

$R^{41}$ represents hydrogen, $C_{1-6}$ alkyl optionally substituted by amino, $C_{1-6}$ alkylamino, di($C_{1-6}$ alkyl)amino, or 2,5-dioxo pyrrolidin-1-yl or a $C_{5-8}$ cycloalkyl optionally substituted by hydroxy, or $R^{40}$ and $R^{41}$ may form, together with adjacent N atom, a 5 to 8 membered saturated hetero-cyclic ring optionally interrupted by O;

$R^{42}$ represents $C_{1-6}$ alkylene optionally substituted by hydroxy or carboxy, or a $C_{5-8}$ cycloalkyl substituted by at least one hydroxy and moreover optionally 1 or 2 substituents selected from the group consisting of hydroxy, amino, oxo and $C_{1-6}$ alkyl, or $R^{41}$ and $R^{42}$ may form, together with adjacent N atom, a 5 to 8 membered saturated heterocyclic ring optionally interrupted by NH or O, wherein said 5 to 8 membered saturated heterocyclic ring is substituted by mono- or di-oxo;

with the proviso that when $R^{41}$ is hydrogen, $C_{1-6}$ alkyl optionally substituted by amino, $C_{1-6}$ alkylamino, or di($C_{1-6}$ alkyl)amino, $R^{42}$ is hydroxy substituted $C_{1-6}$ alkylene or carboxy substituted $C_{1-6}$ alkylene;

$R^{43}$ represents hydrogen, or $C_{1-6}$ alkyl optionally substituted by hydroxy or carboxy;

$R^{44}$ represents $C_{1-6}$ alkyl optionally substituted by hydroxy or carboxy, with the proviso that when $R^{41}$ and $R^{42}$ form, together with adjacent N atom, 5 to 8 membered saturated heterocyclic ring substituted by mono- or di-oxo, $R^{44}$ represents hydroxy substituted $C_{1-6}$ alkyl or carboxy substituted $C_{1-6}$ alkyl;

$R^{45}$, $R^{47}$, $R^{49}$ and $R^{50}$ independently represent hydrogen or $C_{1-6}$ alkyl;

$R^{46}$ and $R^{48}$ independently represent $C_{1-6}$ alkylene optionally substituted hydroxy or carboxy;

n represents an integer selected from 1 to 3;
m represents an integer selected from 0 to 3;

$R^{51}$ represents hydrogen, $C_{1-6}$ alkyl, or a 3 to 8 membered saturated ring optionally interrupted by NH or O;

$R^{52}$ represents hydrogen, $C_{1-6}$ alkoxy carbonyl, or $C_{1-6}$ alkyl substituted by amino, ($C_{1-6}$ alkyl)amino, di($C_{1-6}$ alkyl)amino, N—($C_{1-6}$ alkylsulfonyl)amino, N—($C_{1-6}$ alkanoyl)-amino, $C_{1-6}$ alkoxycarbonyl, tetrazolyl, triazolyl, indolinyl, isoindolinyl, indolyl, isoindolyl, pyrrolidinyl or piperidinyl wherein said pyrrolidinyl and piperidinyl are optionally substituted by mono- or di-oxo, with the proviso that when $R^{51}$ and $R^{52}$ are hydrogen at the same time, $R^3$ is tetrazolyl or $C_{1-6}$ alkanoyl, or when $R^{51}$ is hydrogen or $C_{1-6}$ alkyl, $R^{52}$ is other than hydrogen;

$R^{61}$ and $R^{62}$ independently represent hydrogen or $C_{1-6}$ alkyl optionally substituted by hydroxy, carboxy, phenyl or mono-, di- or tri halogen;

$R^{71}$ represents hydrogen, or $C_{1-6}$ alkyl optionally substituted by amino, hydroxy, carboxy, pyrrolidinyl or piperidinyl, wherein said pyrrolidinyl and piperidinyl are optionally substituted by mono- or di-oxo;

$R^{72}$ represents hydrogen, carboxy, $C_{1-6}$ alkanoyl, amino, ($C_{1-6}$ alkyl)amino, di-($C_{1-6}$alkyl)amino, N—($C_{1-6}$-alkyl)amino carbonyl, $C_{1-6}$ alkyl optionally substituted by hydroxy, carboxy, or mono-, di- or tri-halogen, $C_{1-6}$ alkoxy optionally substituted by mono-, di- or tri-halogen, pyrrolidinyl or piperidinyl, wherein said pyrrolidinyl and piperidinyl are optionally substituted by mono- or di-oxo;

$Z^1$ represents —$[CH_2]_p$—, wherein p represents an integer 1 or 2;

$R^{81}$ represents hydrogen, $C_{1-6}$ alkoxycarbonyl, or $C_{1-6}$ alkyl substituted by pyrrolidinyl or piperidinyl, wherein said pyrrolidinyl and piperidinyl are optionally substituted by mono- or di-oxo;

$R^{82}$ represents hydrogen, hydroxy, carboxy or $C_{1-6}$ alkyl substituted by hydroxy, amino, or carboxy, $R^{83}$ represents hydrogen, hydroxy, carboxy, or $C_{1-6}$ alkyl substituted by hydroxy, amino, or carboxy, with the proviso that when $R^{81}$ is hydrogen, $R^{82}$ or $R^{83}$ is other than hydrogen;

$Z^2$ represents —$[CH_2]_q$—, wherein q represents an integer selected from 0 to 3;

$R^{91}$ represents hydrogen or $C_{1-6}$ alkyl optionally substituted by phenyl;

$R^{111}$ represents hydrogen, carboxy, $C_{1-6}$ alkoxy carbonyl, $C_{1-6}$ alkanoyl, N—($C_{1-6}$-alkyl) aminocarbonyl, $C_{1-6}$ alkoxy optionally substituted by mono-, di- or tri-halogen, or $C_{1-6}$ alkyl optionally substituted by hydroxy, mono-, di- or tri-halogen, amino, ($C_{1-6}$ alkyl)amino, di($C_{1-6}$ alkyl)amino, N—($C_{1-6}$ alkylsulfonyl)amino, N—($C_{1-6}$ alkanoyl)amino, $C_{1-6}$ alkoxycarbonyl, tetrazolyl, triazolyl, indolinyl, isoindolinyl, indolyl, isoindolyl, pyrrolidinyl or piperidinyl, wherein said pyrrolidinyl and piperidinyl are optionally substituted by mono- or di-oxo;

A ring represents a 3 to 8 membered saturated heterocyclic ring, in which the nitrogen atom $N^A$ is the only hetero atom;

B ring represents a 3 to 8 membered saturated heterocyclic ring, in which the nitrogen atom $N^B$ is the only hetero atom;

C ring and D ring together form a 7 to 12 membered diazabicyclic ring; and

E ring represents a 5 to 8 membered saturated heterocyclic ring, in which the nitrogen atom $N^E$ is the only hetero atom.

Yet other preferred compounds of formula (I-b) are those wherein:

$R^1$ represents fluoro, chloro or bromo;
$R^2$ represents fluoro, chloro or bromo;
$R^3$ represents cyano;
$R^4$ represents

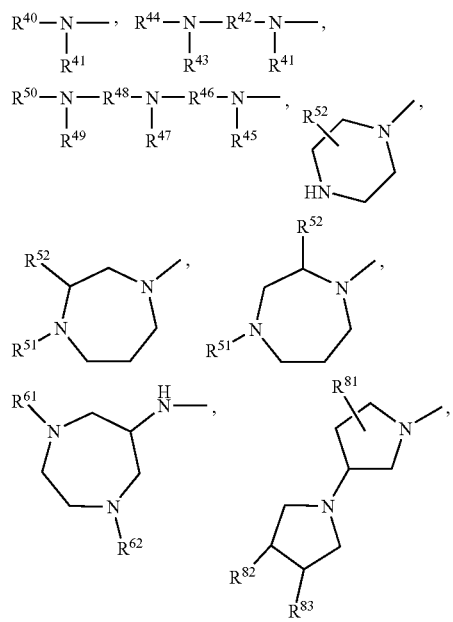

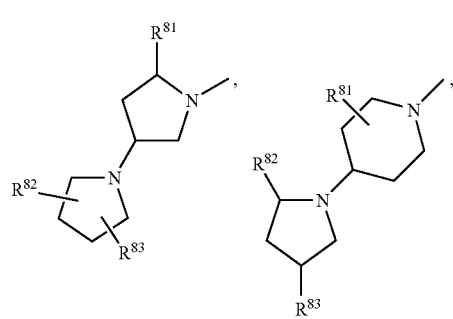

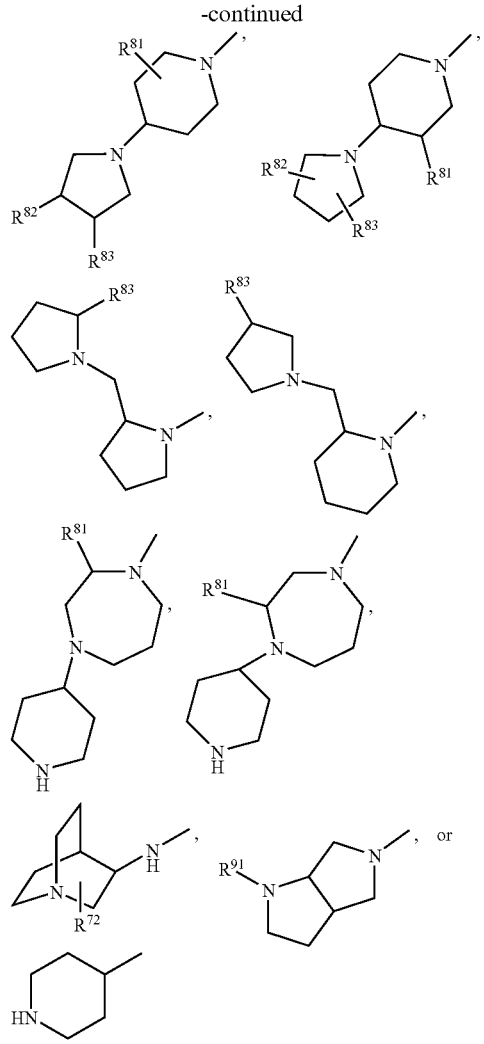

wherein $R^{40}$ represents $C_{1-6}$ alkyl having substituent selected from the group consisting of 2-oxo pyrrolidin-1-yl, 2,5-dioxo pyrrolidin-1-yl, 2-oxo-piperidin-1-yl, 2-oxo-piperidin-3-yl, 4-oxo-piperidin-1-yl, 2-oxo-piperidin-6-yl, 2,5-dioxo-piperidin-1-yl, 2,6-dioxo-piperidin-1-yl, 2,6-dioxo-piperidin-3-yl, piperidin-1-yl, -2-yl, -3-yl or 4-yl (wherein said piperidin is optionally substituted by mono- or di-oxo), hexahydroazepin-1-yl,-2-yl, -3-yl or -4-yl (wherein said hexahydroazepin is optionally substituted by mono- or di-oxo), and 7-oxa-bicyclo[4.1.0]hept-3-yl optionally substituted by amino;

$R^{41}$ represents hydrogen, cyclopentyl or $C_{1-6}$ alkyl optionally substituted by amino, $C_{1-6}$ alkyl amino, di-($C_{1-6}$ alkyl)amino, or 2,5-dioxo pyrrolidin-1-yl, $R^{42}$ represents $C_{1-6}$ alkylene substituted by carboxy or cyclohexyl substituted by mono or di hydroxy, $R^{41}$ and $R^{42}$ may form, together with adjacent N atom, a 5 or 6 membered saturated heterocyclic ring;

$R^{43}$ represents hydrogen or $C_{1-6}$ alkyl optionally substituted by hydroxy, $R^{44}$ represents $C_{1-6}$ alkyl optionally substituted by hydroxy or carboxy, with the proviso that when $R^{41}$ and $R^{42}$ form, together with adjacent N atom, a 5 or 6 membered saturated heterocyclic ring, $R^4$ is hydroxy substituted $C_{1-6}$ alkyl or carboxy substituted $C_{1-6}$ alkyl;

$R^{45}$, $R^{47}$, $R^{49}$ and $R^{50}$ independently represent hydrogen, methyl or ethyl;

$R^{46}$ and $R^{48}$ independently represent $C_{1-6}$ alkylene optionally substituted hydroxy or carboxy;

$R^{51}$ represents hydrogen, cyclopentyl, ethyl or methyl;

$R^{52}$ represents methoxycarbonyl or $C_{1-6}$alkyl substituted by carboxy, amino, methoxy-carbonyl, methanesulfonylamino, acetamido, indolyl, tetrazolyl, 1,2,3-triazolyl, 1,2,4-triazolyl, 1,2,5-triazolyl, 1,3,4-triazolyl, pyrrolidin-1-yl, 2-oxo-pyrrolidin-1-yl, 2,5-dioxo pyrrolidin-1-yl, 2-oxo-piperidin-1-yl, 2-oxo-piperidin-3-yl, 4-oxo-piperidin-1-yl, 2-oxo-piperidin-6-yl, 2,5-dioxo-piperidin-1-yl, 2,6-dioxo-piperidin-1-yl, or 2,6-dioxo-piperidin-3-yl;

$R^{61}$ and $R^{62}$ independently represent benzyl or phenethyl;

$R^{72}$ represents hydrogen, carboxy, $C_{1-6}$ alkanoyl, amino, $(C_{1-6}$alkyl)amino, di-$(C_{1-6}$alkyl)amino, N—$(C_{1-6}$alkyl) amino carbonyl, $C_{1-6}$ alkyl optionally substituted by hydroxy, carboxy, or mono-, di- or tri-halogen, $C_{1-6}$ alkoxy optionally substituted by mono-, di- or tri-halogen, pyrrolidinyl or piperidinyl, wherein said pyrrolidinyl and piperidinyl are optionally substituted by mono- or di-oxo;

$R^{81}$ represents hydrogen, methoxycarbonyl or $C_{1-6}$ alkyl substituted by 2-oxo-pyrrolidin-1-yl, 2,5-dioxo pyrrolidin-1-yl, 2-oxo-piperidin-1-yl, 2-oxo-piperidin-3-yl, 4-oxo-piperidin-1-yl, 2-oxo-piperidin-6-yl, 2,5-dioxo-piperidin-1-yl, 2,6-dioxo-piperidin-1-yl, or 2,6-dioxo-piperidin-3-yl;

$R^{82}$ represents hydrogen, hydroxy or hydroxy substituted $C_{1-6}$ alkyl;

$R^{83}$ represents hydrogen, hydroxy or carboxy;

with the proviso that when $R^{82}$ and $R^{83}$ are hydrogen at the same time, $R^{81}$ is other than hydrogen, or when $R^{81}$ and $R^{83}$ are hydrogen at the same time, $R^{82}$ is other than hydrogen;

$R^{91}$ represents benzyl or phenethyl.

The preferable compounds of the present invention are as follows:

3-(1-Benzyl-hexahydro-pyrrolo[3,4-b]pyrrole-5-sulfonyl)-4-(3,5-dichloro-phenoxy)-benzonitrile;

N-{4-[5-Cyano-2-(3,5-dichloro-phenoxy)-benzenesulfonyl]-piperazin-2-ylmethyl}-methanesulfonamide;

N-{4-[5-Cyano-2-(3,5-dichloro-phenoxy)-benzenesulfonyl]-piperazin-2-ylmethyl}-acetamide;

N-{1-[5-Cyano-2-(3,5-dichloro-phenoxy)-benzenesulfonyl]-piperazin-2-ylmethyl}-methane-sulfonamide;

N-{1-[5-Cyano-2-(3,5-dichloro-phenoxy)-benzenesulfonyl]-piperazin-2-ylmethyl}-acetamide;

4-(3,5-Dichloro-phenoxy)-3-[(3R)-(2-hydroxy-ethylamino)-pyrrolidine-1-sulfonyl]-benzonitrile;

3-(2-Aminomethyl-piperazine-1-sulfonyl)-4-(3,5-dichloro-phenoxy)-benzonitrile dihydrochloride;

1-[5-Cyano-2-(3,5-dichloro-phenoxy)-benzenesulfonyl]-[1,4]diazepane-2-carboxylic acid methyl ester;

4-(3,5-Dichloro-phenoxy)-3-[3(S)-(1H-indol-3-ylmethyl)-piperazine-1-sulfonyl]-benzonitrile;

4-(3,5-Dichloro-phenoxy)-3-[2(S)-(1H-indol-3-ylmethyl)-piperazine-1-sulfonyl]-benzonitrile;

4-(3,5-Dichloro-phenoxy)-3-[2-(2,5-dioxo-pyrrolidin-1-ylmethyl)-piperazine-1-sulfonyl]-benzo-nitrile;

N-{1-[5-Cyano-2-(3,5-dichloro-phenoxy)-benzenesulfonyl]-[1,4]diazepan-2-ylmethyl}-methane-sulfonamide;

1-[4-(3,5-Dichloro-phenoxy)-3-(piperazine-1-sulfonyl)-phenyl]-ethanone;

(R)-N-(1-Aza-bicyclo[2.2.2]oct-3-yl)-5-cyano-2-(3,5-dichloro-phenoxy)-benzenesulfonamide;

(S)-N-(1-Aza-bicyclo[2.2.2]oct-3-yl)-5-cyano-2-(3,5-dichloro-phenoxy)-benzenesulfonamide;

4-(3,5-Dichloro-phenoxy)-3-{4-[(2S)-(1-hydroxy-1-methyl-ethyl)-pyrrolidin-1-yl]-piperidine-1-sulfonyl}-benzonitrile;

4-(3,5-Dichloro-phenoxy)-3-(3-tetrazol-2-ylmethyl-piperazine-1-sulfonyl)-benzonitrile;

4-(3,5-Dichloro-phenoxy)-3-(3-[1,2,4]triazol-1-ylmethyl-piperazine-1-sulfonyl)-benzonitrile;

4-(3,5-Dichloro-phenoxy)-3-(2-[1,2,4]triazol-1-ylmethyl-piperazine-1-sulfonyl)-benzonitrile;

5-Cyano-2-(3,5-dichloro-phenoxy)-N-(2-dimethylamino-ethyl)-N-[2-(2,5-dioxo-pyrrolidin-1-yl)-ethyl]-benzenesulfonamide;

4-(3,5-Dichloro-phenoxy)-3-[3-(2,5-dioxo-pyrrolidin-1-ylmethyl)-piperazine-1-sulfonyl]-benzo-nitrile;

4-(3,5-Dichloro-phenoxy)-3-[3-(2,5-dioxo-pyrrolidin-1-ylmethyl)-4-pyrrolidin-1-yl-piperidine-1-sulfonyl]-benzonitrile;

4-(3,5-Dichloro-phenoxy)-3-{4-[(2S)-hydroxymethyl-pyrrolidin-1-yl]-piperidine-1-sulfonyl}-benzonitrile;

4-(3,5-Dichloro-phenoxy)-3-{(2S)-[(2S)-hydroxymethyl-pyrrolidin-1-ylmethyl]-pyrrolidine-1-sulfonyl}-benzonitrile; and 4-(3,5-Dichloro-phenoxy)-3-(piperidine-4-sulfonyl)-benzonitrile, and their tautomeric and stereoisomeric form, and physiologically acceptable salts thereof.

Alkyl per se and "alk" and "alkyl" in alkylene, alkenyl, alkynyl, alkoxy, alkanoyl, alkylamino, alkylaminocarbonyl, alkylaminosulphonyl, alkylsulphonylamino, alkoxycarbonyl, alkoxy-carbonylamino and alkanoylamino represent a linear or branched alkyl radical having generally 1 to 6, preferably 1 to 4 and particularly preferably 1 to 3 carbon atoms, representing illustratively and preferably methyl, ethyl, n-propyl, isopropyl, tert-butyl, n-pentyl and n-hexyl.

Alkoxy illustratively and preferably represents methoxy, ethoxy, n-propoxy, isopropoxy, tert-butoxy, n-pentoxy and n-hexoxy.

Alkylamino illustratively and preferably represents an alkylamino radical having one or two (independently selected) alkyl substituents, illustratively and preferably representing methylamino, ethylamino, n-propylamino, isopropylamino, tert-butylamino, n-pentylamino, n-hexyl-amino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Cycloalkyl per se and in cycloalkylamino and in cycloalkylcarbonyl represents a cycloalkyl group having generally 3 to 8 and preferably 5 to 7 carbon atoms, illustratively and preferably representing cyclopropyl, cyclobutyl, cyclopentyl, cyclohexyl and cycloheptyl.

Heterocyclyl per se and in heterocyclic represents a mono- or polycyclic, preferably mono- or bicyclic, nonaromatic heterocyclic radical having generally 4 to 10 and preferably 5 to 8 ring atoms and up to 3 and preferably up to 2 hetero atoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two hetero atoms selected from the group consisting of O, N and S.

EMBODIMENT OF THE INVENTION

The compound of the formula (I) of the present invention can be, but not limited to be, prepared by combining various conventional methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis ($3^{rd}$ Edition)" by Greene and Wuts.

The compound represented by the general formula (I-i), (I-ii) and (I-iii) of the present invention can be, but not limited to be, prepared by using the Method [A], [B] and [C] below respectively.

above or protected $R^3$ and $R^{4'}$ is the same as $R^4$ as defined above or protected $R^4$) can be prepared by the following procedures in three or four steps;

In the Step A-1, the compound of the formula (2) (wherein X, $R^1$, $R^2$ and $R^{3'}$ are same as defined above) can be obtained by the reaction of the compound of the formula (1) (wherein L represents leaving group, for instance, halo group (fluorine, chlorine, bromine, or iodine), sulfonates (e.g., mesylate, tosylate or triflate); and the like) with the compound of the formula (4) (wherein X, $R^1$ and $R^2$ are same as defined above) in solvent.

Examples of the solvent include, for instance, halogenated hydrocarbons such as dichloromethane, chloroform and 1,2-dichloroethane; ethers such as diethyl ether, isopropyl ether, dioxane, tetra-hydrofuran (THF) and 1,2-dimethoxyethane; nitriles such as acetonitrile; amides such as N,N-dimethylformamide (DMF), N,N-dimethylacetamide and N-methylpyrrolidone; sulfoxides such as dimethyl sulfoxide, and others.

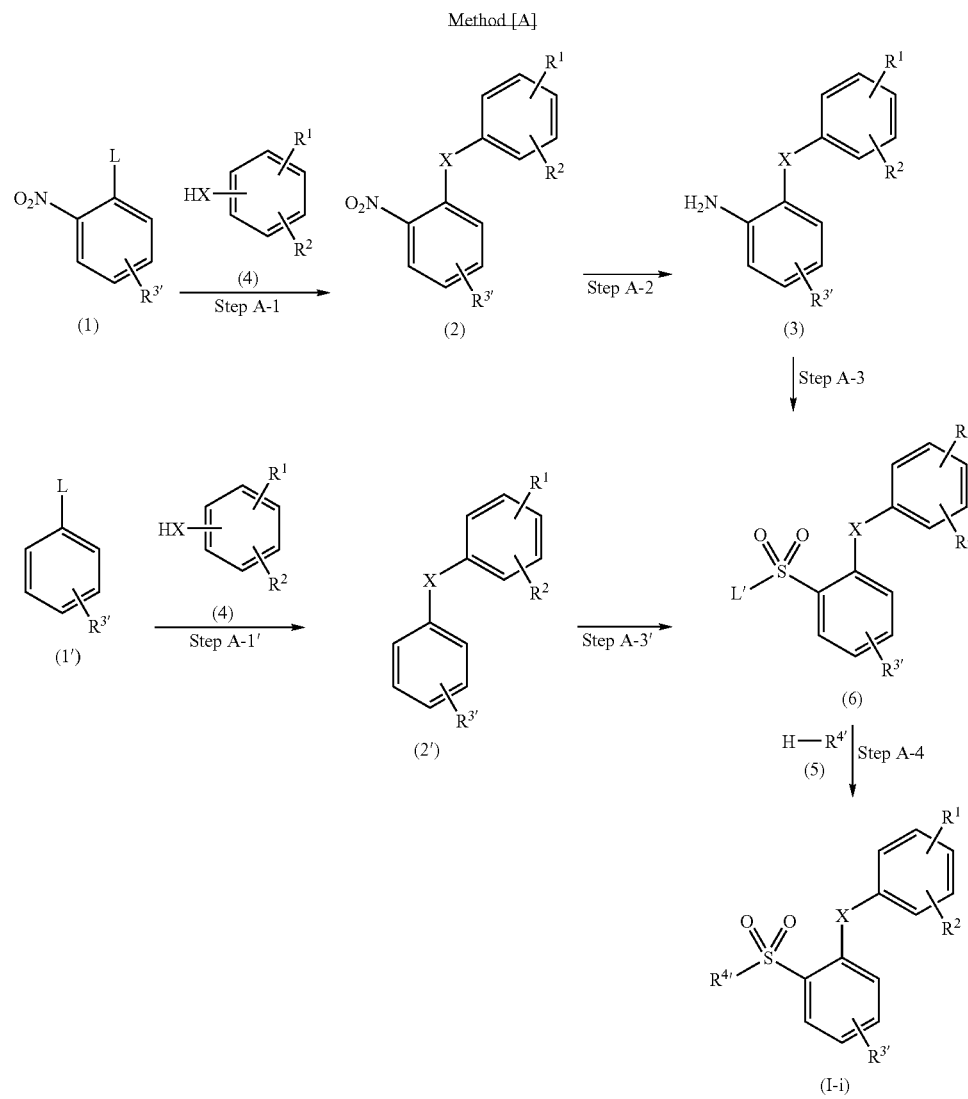

In the Method [A], the compound of the formula (I-i)(X, $R^1$ and $R^2$ are as defined above, $R^{3'}$ is the same as $R^3$ as defined Optionally, two or more of the solvents selected from the listed above can be mixed and used.

The reaction temperature is usually, but not limited to, about −10° C. to 200° C., and preferably about 10° C. to 80° C. The reaction may be carried out for, usually, 30 minutes to 48 hours and preferably 1 hour to 24 hours.

The reaction can be advantageously conducted in the presence of a base. The examples of the base include an alkali metal hydride such as sodium hydride or potassium hydride; alkali metal alkoxide such as sodium methoxide, sodium ethoxide and potassium tert-butoxide; alkali metal hydroxide such as sodium hydroxide and potassium hydroxide; carbonates such as sodium carbonate and potassium carbonate; alkali metal hydrogen carbonates such as sodium hydrogen carbonate and potassium hydrogen carbonate; organic amines such as pyridine, triethylamine and N,N-diisopropylethylamine, and others.

In the Step A-2, the compound of the formula (3) (wherein X, $R^1$, $R^2$ and $R^{3'}$ are same as defined above) can be obtained by the reduction of the compound of the formula (2) (wherein X, $R^1$, $R^2$ and $R^{3'}$ are same as defined above) with stannous chloride or iron powder with an acid (e.g., hydrochloric acid) in solvent such as ethyl acetate, water and others.

The compound of the formula (3) (wherein X, $R^1$, $R^2$ and $R^{3'}$ are same as defined above) can be also obtained by the hydrolysis of the compound of the formula (2) (wherein X, $R^1$, $R^2$ and $R^{3'}$ are same as defined above).

In the Step A-3, the compound of the formula (6) (wherein X, $R^1$, $R^2$ and $R^{3'}$ are same as defined above and L' represents leaving group, for instance, halo group (fluorine, chlorine, bromine, or iodine); and the like) can be prepared from the compound of the formula (3) (wherein X, $R^1$, $R^2$ and $R^{3'}$ are same as defined above) in two steps.

First, the compound of the formula (3) (wherein X, $R^1$, $R^2$ and $R^{3'}$ are same as defined above) is treated with an acid (e.g., hydrochloric acid) and sodium nitrite in a solvent (e.g., water, acetic acid) at about −20° C. to 0° C.

Then, the reaction mixture is added to the solution of sulfur dioxide in acid such as acetic acid and the like.

Examples of the solvent include, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; nitriles such as acetonitrile; amides such as N,N-dimethylformamide (DMF), N,N-dimethylacetamide and N-methylpyrrolidone; water and others. Optionally, two or more of the solvents selected from the listed above can be mixed and used.

The reaction temperature is usually, but not limited to about −10° C. to 200° C., and preferably about 0° C. to 30° C. The reaction may be carried out for, usually, 30 minutes to 48 hours and preferably 1 to 24 hours.

The reaction can be carried out in the presence of a catalyst, including for instance, cooper salts such as copper chloride and others.

In the Step A-4, the compound of the formula (I-i) (wherein X, $R^1$, $R^2$, $R^{3'}$ and $R^{4'}$ are as defined above) can be obtained by the reaction of the compound of the formula (6) (wherein X, L', $R^1$, $R^2$ and $R^{3'}$ are same as defined above) with the compound of the formula (5) (wherein $R^{4'}$ is same as defined above) in a similar manner described in Step A-1 of Method [A] for the preparation of the compound of (2).

The compound (I-i) can be further reacted to remove protecting group of $R^{3'}$ or $R^{4'}$.

The compound of the formula (6) can also be prepared by the procedures of step A-1' and step A-3' with starting compound (1') (wherein L and $R^{3'}$ are same as defined above).

In the Step A-1', the compound of the formula (2') (wherein X, $R^1$, $R^2$, and $R^{3'}$ are same as defined above) can be prepared from the compound of the formula (1') (wherein L and $R^{3'}$ are same as defined above), instead of the compound of the formula (1), in a similar manner described in the Step A-1 for preparation of the compound of the formula (2) by using a compound of the formula (4) (wherein X, $R^1$ and $R^2$ are same as defined above).

In the Step A-3', the compound of the formula (6) (wherein X, $R^1$, $R^2$, $R^{3'}$ and L' are same as defined above) can be prepared with the compound of the formula (2') (wherein X, $R^1$, $R^2$, and $R^3$ are same as defined above) with sulfonic acid halide (e.g., chlorosulfonic acid). The reaction can be carried out without solvent or in solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; amides such as N,N-dimethyl-formamide (DF), N,N-dimethylacetamide and N-methylpyrrolidone; sulfoxides such as dimethylsulfoxide (DMSO); and others. Optionally, two or more of the solvents selected from the listed above can be mixed and used.

The reaction temperature is usually, but not limited to about −10° C. to 200° C., and preferably about 0° C. to 170° C. The reaction may be carried out for, usually, 30 minutes to 48 hours and preferably 1 to 24 hours.

The compound of the formula (1), (1'), (4) and (5) are commercially available or can be prepared by the conventional reactions.

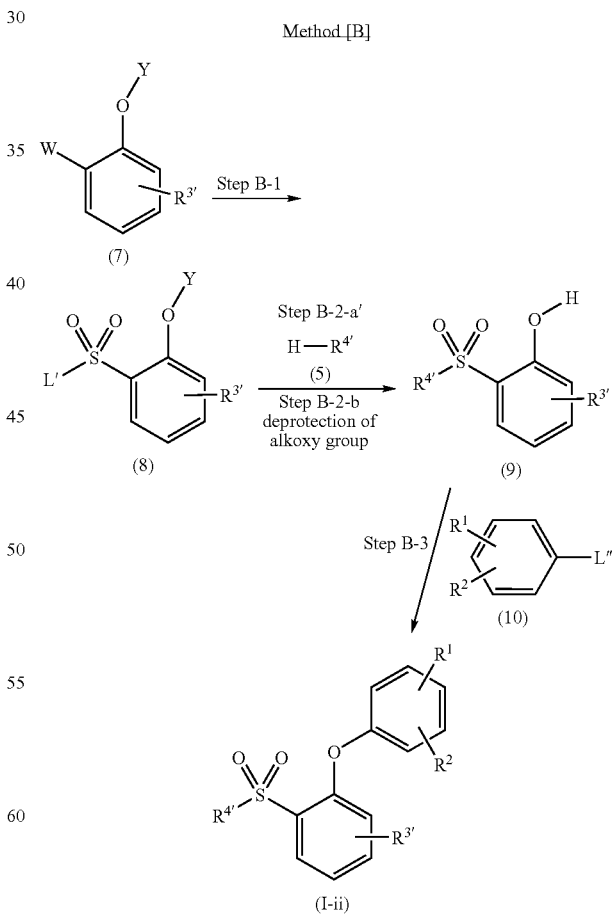

The compound of the formula (I-ii) ($R^1$ and $R^2$ are as defined above, $R^{3'}$ is the same as $R^3$ as defined above or protected $R^3$ and $R^{4'}$ is the same as $R^4$ as defined above or protected $R^4$) can be prepared by the following procedures in three steps;

In the Step B-1, the compound of the formula (8) (wherein L' and $R^{3'}$ are same as defined above and Y represents $C_{1-6}$ alkyl) can be obtained by the reaction of the compound of the formula (7) (wherein Y and $R^{3'}$ are same as defined above and W represents hydrogen, amino, and the like) in a similar manner described in Step A-3 or A-3' of Method [A] for the preparation of the compound of the formula (6).

In the Step B-2, the compound of the formula (9) (wherein $R^{3'}$ and $R^{4'}$ are same as defined above) can be prepared from the compound of the formula (8) in two steps; (step B-2-a) the reaction with H—$R^{4'}$ and (step B-2-b) deprotection of alkoxy group.

In the Step B-2-a, the reaction of compound of the formula (8) (wherein Y, L' and $R^{3'}$ are same as defined above) with the compound of formula (5) (wherein $R^4$ is same as defined above) can be performed in a similar manner as described in the step A-4 of method A for the preparation of compound of the formula (I-i).

In the Step B-2-b, the successive deprotection of alkoxy group to obtain the compound of formula (9) (wherein $R^{3'}$ and $R^{4'}$ are same as defined above) can be done by the reaction with Lewis acid such as, for example, $BBr_3$, in a solvent including, for instance, halogenated hydrocarbons such as dichloromethane, chloroform and 1,2-dichloroethane; and others. Optionally, two or more of the solvents selected from the listed above can be mixed and used.

The reaction temperature is usually, but not limited to about −30° C. to 200° C., and preferably about −10° C. to 80° C. The reaction may be carried out for, usually, 30 minutes to 48 hours and preferably 1 hour to 24 hours.

In the Step B-3, the compound of the formula (I-ii) (wherein $R^1$, $R^2$, $R^{3'}$ and $R^{4'}$ are as defined above) can be obtained by the reaction of the compound of the formula (9) (wherein $R^{3'}$ and $R^{4'}$ are same as defined above) with the compound of the formula (10) (wherein $R^1$ and $R^2$ are same as defined above and L" represents leaving group, such as boronic acid, halogen atom e.g., fluorine, chlorine, bromine, or iodine atom).

The reaction can be performed in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethyl-formamide (DMF), N,N-dimethylacetamide and N-methylpyrrolidone; sulfoxides such as dimethyl sulfoxide, and others. Optionally, two or more of the solvents selected from the listed above can be mixed and used.

The reaction temperature is usually, but not limited to about −10° C. to 200° C., and preferably about 10° C. to 100° C. The reaction may be carried out for, usually, 30 minutes to 48 hours and preferably 1 hour to 24 hours.

The reaction can be carried out in the presence of a catalyst, including for instance, cooper salts such as cooper (II) acetate, palladium salts such as palladium (II) acetate, and others. The reaction can be advantageously conducted in the presence of a base. The examples of the base include an alkali metal alkoxide such as sodium methoxide, sodium ethoxide and potassium tert-butoxide; alkali metal hydroxide such as sodium hydroxide and potassium hydroxide; carbonates such as cesium carbonate, sodium carbonate and potassium carbonate; alkali metal hydrogen carbonates such as sodium hydrogen carbonate and potassium hydrogen carbonate; organic amines such as pyridine, triethylamine and N,N-diisopropylethylamine, and others.

The compound (I-ii) can be further reacted to modify $R^{3'}$ or $R^{4'}$, e.g. to deprotect.

The compounds of the formula (7) and (10) are commercially available or can be prepared by conventional reactions.

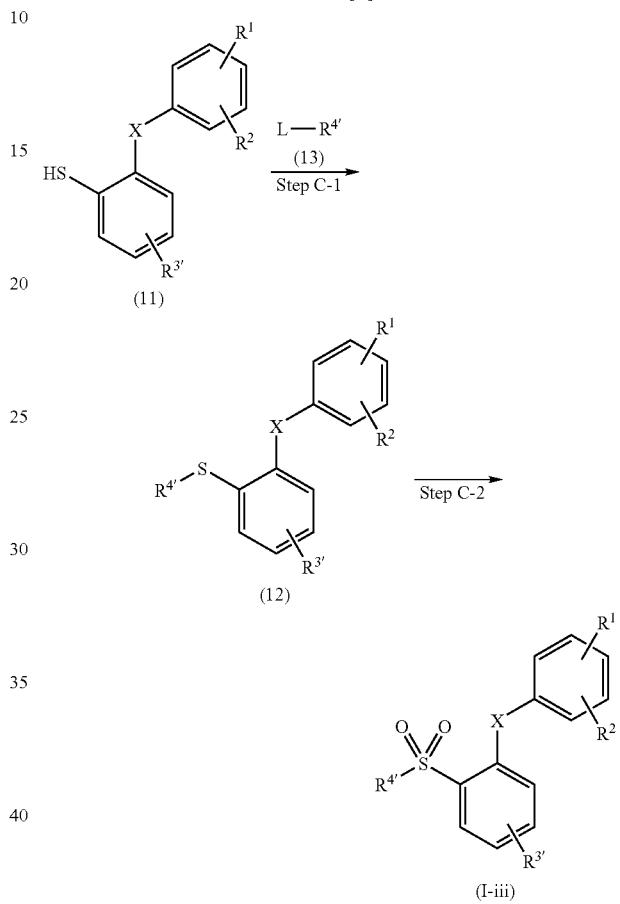

Method [C] is especially advantageous when $R^4$ of the formula (I) represents E ring defined above, hereinafter $R^{4''}$ of the formula (1-iii) represents E ring with substituent $R^{111}$ as defined in $R^4$ or protected thereof.

The compound of the formula (I-iii) (wherein X, $R^1$, $R^2$, $R^{3'}$ and $R^{4''}$ are same as defined above) can be prepared by the following procedures in two steps;

In the Step C-1, the compound of the formula (12) (wherein X, $R^1$, $R^2$, $R^{3'}$ and $R^{4''}$ are same as defined above) can be obtained by the reaction of the compound of the formula (11) (wherein X, $R^1$, $R^2$ and $R^{3'}$ are same as defined) with the compound of the formula (13) (wherein $R^{4''}$ are same as defined above and L represents leaving group defined above) using a base such as alkali metal carbonates (eg, sodium carbonate, potassium carbonate and the like), triethylamine, potassium hydroxide, and others.

The reaction can be performed in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethyl-formamide (DMF), N,N-dimethylacetamide and N-methylpyrrolidone; sulfoxides such as dimethyl sulfoxide, and others. Optionally, two or more of the solvents selected from the listed above can be mixed and used.

The reaction temperature is usually, but not limited to about −10° C. to 200° C., and preferably about 10° C. to 100° C. The reaction may be carried out for, usually, 30 minutes to 48 hours and preferably 1 hour to 24 hours.

In the Step C-2, the compound of the formula (1-iii) (wherein X, $R^1$, $R^2$, $R^{3'}$ and $R^{4''}$ are same as defined above) can be obtained by the treatment of the compound of the formula (12) (wherein X, $R^1$, $R^2$, $R^{3'}$ and $R^{4''}$ are same as defined above) under suitable oxidizing conditions, such as hydrogen peroxide, sodium periodate, m-chloroperbenzoic acid (m-CPBA), potassium permanganate and others in the presence of or without catalyst, such as catalytic ruthenium trichloride in solvent including, for instance, water, halogenated hydrocarbons such as, methylene chloride, carbon tetrachloride, chlorobenzene, dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide and N-methyl-pyrrolidone; and others. Optionally, two or more of the solvents selected from the listed above can be mixed and used.

The reaction temperature is usually, but not limited to about −10° C. to 200° C., and preferably about 10° C. to 50° C. The reaction may be carried out for, usually, 30 minutes to 48 hours and preferably 1 hour to 20 hours.

The compound (1-iii) can be further reacted to remove protection group of $R^{3'}$ or $R^{4''}$.

The compound of the formula (11) and (13) are commercially available or can be prepared by the conventional reactions.

When the compound shown by the formula (I) or a salt thereof has tautomeric isomers and/or stereoisomers (e.g, geometrical isomers and conformational isomers), each of their separated isomer and mixtures are also included in the scope of the present invention.

When the compound shown by the formula (I) or a salt thereof has an asymmetric carbon in the structure, their optically active compounds and racemic mixtures are also included in the scope of the present invention.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydroiodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or a salts thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically acceptable excipients. Excipients are inert substances such as, without limitation carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically acceptable excipients therefore. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, acacia, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described in detail below in the form of examples, but they should by no means be construed as defining the metes and bounds of the present invention.

In the examples below, all quantitative data, if not stated otherwise, relate to percentages by weight.

$^1$H NMR spectra were recorded using either Bruker DRX-300 (300 MHz for $^1$H) spectrometer in $CDCl_3$. Chemical shifts are reported in parts per million (ppm) with tetramethylsilane (TMS) as an internal standard at zero ppm. Coupling constant (J) are given in hertz and the abbreviations s, d, t, q, m, and br refer to singlet, doublet, triplet, quartet, multiplet, and broad, respectively. Mass spectroscopy data were recorded on a FINNIGAN MAT 95. TLC was performed on a precoated silica gel plate (Merck silica gel 60 F-254). Silica gel (WAKO-gel C-200 (75-150 m)) was used for all column chromatography separations. Z in the table 1 represents decomposition.

All chemicals were reagent grade and were purchased from Sigma-Aldrich, Wako pure chemical industries, Ltd., Tokyo kasei kogyo Co., Ltd., Nacalai tesque, Inc., Watanabe Chemical Ind. Ltd., Maybridge plc, Lancaster Synthesis Ltd., Merck KgaA, Kanto Chemical Co., Ltd.

The effects of the present compounds were examined by the following assays and pharmacological tests.

[Determination of IC50 Values of Compounds in Receptor Binding Assay]

(1) Cell

Human CCR3-transformed K562 cells were used. The cloned CCR3 cDNA was constructed with pcDNA3 vector and transfected into a K562 cell line. The human CCR3-transformed K562 cells were maintained in RPMI-1640 (Cat.#22400-089, Life Technologies) supplemented with 10% FCS (Cat.#A-1115-L, Hyclone), 55 µM 2-mercaptoethanol (Cat.#21985-023, Life Technologies), 1 mM sodium pyruvate (Cat.#11360-070, Life Technologies), 100 units/ml of penicillin G and 100 µg/ml of streptomycin (Cat.#15140-122, Life Technologies), and 0.4 mg/ml of Geneticin (Cat.#10131-035, Life Technologies)(hereinafter called "culture medium"). Before the receptor binding assay, cells were pretreated with 5 mM sodium butyrate (Cat.#193-01522, Wako)-containing the culture medium ($2 \times 10^5$ cells/ml) for 20-24 hours to increase the expression of CCR3.

(2) Receptor Binding Assay

Butyrate-pretreated cells, suspended in binding buffer (25 mM HEPES pH 7.6, 1 mM $CaCl_2$, 5 mM $MgCl_2$, 0.5% BSA, 0.1% $NaN_3$) at a cell density of $2 \times 10^6$ cells/ml, were added into 60 µl/well in the 96-well round bottom polypropylene plate (Cat.#3365, Costar). Compounds, diluted with the binding buffer (4-times higher concentration of the final concentration), were added into 30 µl/well in the polypropylene plate. [$^{125}$I]-labeled human eotaxin (Cat.#IM290, Amersham Pharmacia Biotech), diluted with the binding buffer at the concentration of 0.4 nM (final concentration; 0.1 nM), was added into 30 µl/well in the polypropylene plate. Total 120 µl/well of binding reaction mixture (60 µl/well of cell suspension, 30 µl/well of compound solution, and 30 µl/well of [$^{125}$I]-labeled eotaxin) were incubated in the polypropylene plate for 1 hour at room temperature after the incubation, 100 µl/well of the reaction mixture was transferred to a filtration plate, (Cat.#MAFB-N0B, Millipore), and washed with the washing buffer (25 mM HEPES pH 7.6, 1 mM $CaCl_2$, 5 mM $MgCl_2$, 0.5% BSA, 0.1% $NaN_3$, 0.5 M NaCl) twice. The 96-well filtration plate was pretreated with 100 µl/well of 0.5% polyethylenimine (Cat.#P-3143, Sigma) for 2-4 hours at room temperature and washed with the washing buffer twice before use. The non-specific binding was determined by parallel incubation in the presence of 500 nM of non-labeled eotaxin (Cat.#23209, Genzyme Techne). The radioactivities remained on the filter were measured by liquid scintillation counter (TopCount™, Packard) after an addition of 45 µl/well of scintillant (Microscint20, Cat.#6013621, Packard). The inhibition percent at each concentration of compound was calculated, and IC50 values were determined from the inhibition curve.

[Determination of IC50 Values of Compounds in Calcium Mobilization Assay]

(1) Cell

Human CCR3-transformed K562 cells were used. The human CCR3-transformed K562 cells were maintained in RPMI-1640 supplemented with 10% FCS, 55 μM 2-mercaptoethanol (Cat.#21985-023, Life Technologies), 1 mM sodium pyruvate, 100 units/ml of penicillin G and 100 μg/ml of streptomycin, and 0.4 mg/ml of Geneticin. Before the calcium mobilization assay, cells were pretreated with 5 mM sodium butyrate-containing the culture medium ($2 \times 10^5$ cells/ml) for 20-24 hours to increase the expression of CCR3.

(2) Calcium Mobilization Assay

Butyrate-pretreated cells were loaded with Fluo-3AM (Cat.#F-1242, Molecular Probes) in loading buffer (Hanks' solution Cat.#05906 Nissui, 20 mM HEPES pH 7.6, 0.1% BSA, 1 mM probenecid Cat.#P-8761 Sigma, 1 μM Fluo-3AM, 0.01% pluronic F-127 Cat.#P-6866 Molecular Probes) at a cell density of $1 \times 10^7$ cells/ml. Then, cells were washed with calcium assay buffer (Hanks' solution Cat.#05906 Nissui, 20 mM HEPES pH 7.6, 0.1% BSA, 1 mM Probenecid Cat.#P-8761 Sigma). The cell suspension ($3.3 \times 10^6$ cells/ml) was added into 60 μl/well in the 96 well clear bottom black plate (Cat.#3904, Costar). Compounds, diluted (5-times concentration of the final concentration) with the calcium assay buffer, were added into 20 μl/well in the plate 10 minutes before assay. Human recombinant eotaxin, diluted with the calcium assay buffer at the concentration of 50 nM (final concentration; 10 nM), was added into in a polypropylene plate (Cat.#3365, Costar). Mobilization of cytoplasmic calcium was measured by FDSS-6000 or FDSS-3000 (Hamamatsu Photonics) over 60 sec after the stimulation with 10 nM eotaxin. The inhibition percent at the each concentration of compound was calculated, and IC50 values were determined from the inhibition curve.

[Determination of IC50 Values of Compounds in Chemotaxis Assay]

(1) Cell

Human CCR3-transformed L1.2 cells were used. Human CCR3-expressing L1.2 stable transformant was established by electroporation, referring to the methods described in J. Exp. Med. 183:2437-2448, 1996. The human CCR3-transformed L1.2 cells were maintained in RPMI-1640 supplemented with 10% FCS, 100 units/ml of penicillin G and 100 μg/ml of streptomycin, and 0.4 mg/ml of Geneticin. One day before the chemotaxis assay, cells were pretreated with 5 mM sodium butyrate-containing culture medium ($5 \times 10^5$ cells/ml) for 20-24 hours to increase the expression of CCR3.

(2) Chemotaxis Assay

Butyrate-pretreated cells were suspended in chemotaxis buffer (Hanks' solution Cat.#05906 Nissui, 20 mM HEPES pH 7.6, 0.1% human serum albumin Cat.#A-1887 Sigma) at a cell density of $1.1 \times 10^7$ cells/ml. A mixture of 90 μl of cell suspension and 10 μl of compound solution diluted with chemotaxis buffer (10-times concentration of the final concentration) were preincubated for 10 minutes at 37° C. The mixture of cells and compounds was added into the upper chamber of the 24-well chemotaxis chamber (Transwell™, Cat.#3421, Costar, pore size; 5 μm). 0.5 ml of 10 nM of human recombinant eotaxin (Cat.#23209, Genzyme Techne) solution, diluted with chemotaxis buffer, was added into the lower chamber of the chemotaxis plate. Then, chemotaxis was performed in $CO_2$ incubator at 37° C. for 4 hours. After 4 hrs incubation, migrated cells were counted using FACScan (Becton Dickinson). The inhibition percent at the each concentration of compound was calculated, and IC50 values were determined from the inhibition curve.

[Selectivity Test]

Selectivity test was done in calcium mobilization assay and in receptor binding assay by using CCR1, CCR2, CCR4, CCR5, CCR7, CCR8, CXCR1 and PAR-1 (peptidase activate receptor) stable transformants. Methods for the test are the same as that of CCR3. Only the difference is that different stable transformants were used for these selectivity tests.

[Determination of IC50 Values of Compounds in Chemotaxis Assay with the use of Human Eosinophils]

Human eosinophils were purified from peripheral blood. Twenty five ml of heparinized blood was layered on 15 ml of Mono-Poly Resolving Medium (#16-980-49DN, ICN Biomedicals Co. Ltd, Japan) in 50 ml tube (#2335-050, Iwaki, Japan) gently and then centrifuged at 400G, for 20 min, at room temperature. After centrifugation, red blood cells were removed by hypotonic lysis. The polymorphonuclear leukocyte pellet was incubated with anti-human CD16 Microbeads (#130-045-701, Milteynyi Biotec GmbH, Germany) for 30 min at 4° C. After washing the cells, magnetically labeled neutrophils were then depleted by applying the cell suspension to BS columns (#130-041-304, Milteynyi Biotec GmbH, Germany) attached to VarioMACS (#130-090-282, Milteynyi Biotec GmbH, Germany).

Chemotaxis assay with the use of the obtained eosinophils was done by the same protocols as that using CCR3 stable transformants, L1.2 cells.

[Primate Chronic Asthma Model: Protocol]

Materials and Methods: The animals used in this study were wild caught, adult male cynomolgus monkeys (*Macaca fascicularis*) weighing 4.0 to 9.0 kg (Charles River BRF, Inc.). All animals studied demonstrated a naturally occurring respiratory sensitivity to inhaled *Ascaris suum* extract. Animals were housed individually in environmentally controlled rooms in open mesh cages and provided food twice daily and water ad libitum. Each animal was fasted for approximately 12 hours prior to the day of study. For each study the animals were anesthetized with ketamine hydrochloride (7 mg/kg, i.m.; Ketaset, Fort Dodge, Iowa) and xylazine (1.2 mg/kg, i.m.; Bayer Corp., Elkart, Ind.), incubated with a cuffed endotracheal tube (5.0 mm ID; Mallinckrodt Critical Care, Glen Falls, N.Y.) and seated in a specially designed support chair. Ketamine (5 mg/kg, i.m.) was used to supplement anesthesia as needed.

Study Protocol: Airway responsiveness (AR) to inhaled methachroline followed by bronchoalveolar lavage (BAL) to assess airway cellular composition (ACC) were determined 3 days before (day 0) and 3 days after (day 10) three alternate-day (days 3,5,7) inhalations of *Ascaris suum* extract. Animals were rested 6 to 8 weeks between studies to allow airway responsiveness and inflammation to return to baseline (pre-antigen) levels. Treatment studies were bracketed by vehicle control studies to assure that no changes in sensitivity to antigen occurred over time.

The test compounds dissolved in Ethanol:PEG400:Water (10:50:40 v/v) were administered under light anesthetisia.

Aerosol Delivery System and Inhalation Challenges: Aerosol inhalation challenges were administered by intermittent positive pressure breathing with a Bird Mark 7A respirator and micronebulizer (model 8158). Each challenge consisted of 30 breaths (maximum inspiratory pressure=20 cmH$_2$O). *Ascaris suum* extract (Greer Laboratories, Lenoir, N.C.) was diluted with PBS to a final threshold concentration previously determined for each animal and administered as an aerosol (particle size <2 µm). Methacholine (Sigma Chemical Co, St. Louis, Mo.) was dissolved in PBS at a concentration of 100 mg/ml and serial dilutions of 30, 10, 3, 1, 0.3 and 0.1 mg/ml were subsequently prepared for nebulization.

Measurement of Respiratory System Resistance (Rrs): The animal was connected to a Harvard Ventilator (Harvard Apparatus, S. Natick, Mass.) via the endotracheal tube and ventilated at a rate between 30-35 breaths per minute. Airflow was measured by a Fleisch (Hans Rudolph) pneumotachograph and thoracic pressure was measured by a validyne pressure transducer (as the difference between the pressure at the distal end of the endotracheal tube and room pressure). The pneumotachograph and validyne were connected to a pre-amplifier and then into an MI$^2$ respiratory analyzer (Malvern, Pa.). Using the primary signals of flow and pressure the analyzer computed airway resistance and compliance (as well as a number of other respiratory parameters).

Methacholine Dose Response Determinations: To assess airway responsiveness to inhaled methacholine, cumulative dose response curves were constructed by administering increasing concentrations of methacholine until increases in Rrs of between 100 and 200% were obtained. A vehicle control challenge was performed prior to the first dose of methacholine. Changes in Rrs were measured continuously over a 10 minute period post aerosol challenge. Aerosol challenges were separated by 5 to 10 minutes or until Rrs returned to baseline values.

Determination of PPC$_{100}$ Values: The resistance obtained with PBS was set as zero. The percentage increase in resistance above zero at each dose of methacholine was entered into the computer and the program used an algorithm to determine the exact methacholine concentration which caused an increase in resistance of 100% above baseline (PC$_{100}$). Differences (day 10-day 0) in PC$_{100}$ values were calculated as logs (base 10) to normalize the data and account for the large variation in absolute values for the PC$_{100}$ between animals.

Bronchoalveolar Lavage: Following methacholine dose response determinations each monkey was placed in the supine position and a fiberoptic bronchoscope (Olympus Optical, model 3C-10, Lake Success, N.Y.) was guided past the carina and wedged into a fifth to seventh generation bronchus. A total of 15 ml of bicarbonate buffered saline (pH 7.4) was infused and gently aspirated through a channel in the bronchoscope. Collected samples were immediately centrifuged at 2000 rpm for 10 minutes at 4° C. The resulting pellets were resuspended in Ca++ and Mg++ free Hank's balanced salt solution. To avoid possible effects of the BAL procedure on lung cellular composition, BAL was performed on alternating right and left lungs. Total white cells per milliliter of BAL fluid was obtained using a Coulter counter (Coulter Corp., Miami, Fla.). BAL cell composition was determined by counting a minimum of 200 cells from a Wright's stained cytospin slide preparation.

Blood Samples: Blood samples were collected prior to and 30 minutes, 1 hr and 2 hr after the first dose of the test compounds (morning of day 2), immediately before each subsequent dose, and 30 minutes, 1 hr and 2 hr after the final dose (evening of day 9). Blood was collected from the femoral vein into EDTA, centrifuged at 1500 rpm for 15 minutes at 4° C. and the plasma stored at −70° C. until assayed for the test compounds.

Statistical Analysis: All data were evaluated statistically with the use of students t-test where a p value <0.05 was considered statistically significant.

Results of receptor binding assay (RBA), Ca$^{2+}$ mobilization assay (Ca$^{2+}$) are shown in Examples and tables of the Examples below. The data corresponds to the compounds as yielded by solid phase synthesis and thus to levels of purity of about 40 to 90%. For practical reasons, the compounds are grouped in three classes of activity as follows:

$IC_{50}=A100$ nM$<B500$ nM$<C$

The Compounds of the Present Invention Also Show More than 100-Fold Selectivity Against CCR1, CCR5, CCR7, CCR8 and CXCR1 in receptor binding assays.

The compounds of the present invention show dose-dependent inhibitory effect on eotaxin-induced chemotaxis of human eosinophils and strong activity in vivo assays.

Procedure for Starting Compound

[Starting Compound A]

5-cyano-2-(3,5-dichlorophenoxy)phenylsulfonyl-chloride

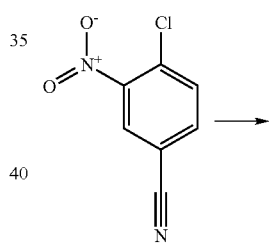

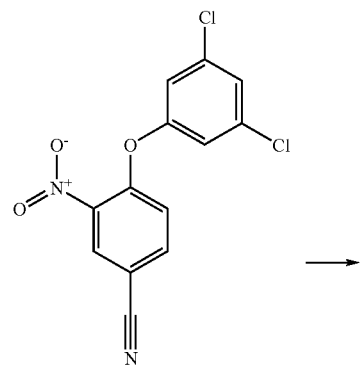

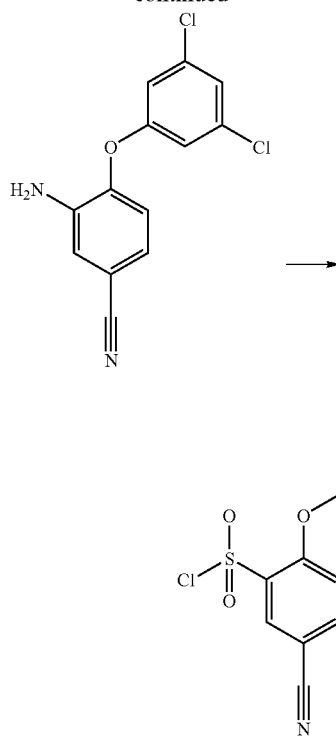

(1) To a mixture of 4-chloro-3-nitro-benzonitrile (24.0 g, 131 mmol) and 3,5-dichloro-phenol (32.0 g, 197 mmol) in dry THF (150 ml) was added NaH (6.84 g, 171 mmol) in portions and the mixture was refluxed for 1 hour. After cooled to room temperature, the solvent was evaporated, and 100 ml of ice water and 20 ml of 4N NaOH aq. were added to the residue. The precipitate was collected by filtration, washed with 0.5 N NaOH aq. and water, dried in vacuo to give the 5-cyano-2-3,5-dichlorophenoxy)nitrobenzene (40.0 g, 98.4%) as slight yellow solid.

(2) The mixture of 5-cyano-2-(3,5-dichlorophenoxy) nitrobenzene (4.08 g, 13.20 mmol) and Tin (II) chloride dihydrate (17.87 g, 79.20 mmol) in EtOAc (200 mL) was heated to reflux for 2 hours. After cooled to room temperature, the reaction mixture was poured into sat. NaHCO$_3$ aq. The mixture was extracted with EtOAc. The extract was washed with brine, and dried over MgSO$_4$. The solvent was evaporated in vacuo to give 5-cyano-2-(3,5-dichlorophenoxy)aniline (3.53 g, 95.8%).

(3) 5-cyano-2-(3,5-dichlorophenoxy)aniline (3.53 g, 12.65 mmol) was dissolved in the mixture of conc. HCl aq. (6.33 ml) and HOAc (2.53 ml). The solution was cooled to 0° C. and sodium nitrite (0.96 g, 13.9 mmol) in water (1.27 ml) was added dropwise with stirring. After 30 minutes, the reaction mixture was added dropwise to the suspended mixture of CuCl (0.63 g, 6.32 mmol) in saturated solution of SO$_2$ in HOAc (25.3 ml) at 5° C. The reaction mixture was stirred for 30 minutes at 10° C., and poured into water. The resulting mixture was extracted with EtOAc. The extract was washed with sat. NaHCO$_3$ aq., brine, and dried over MgSO$_4$. The solvent was evaporated in vacuo to give 5-cyano-2-(3,5-dichlorophenoxy) phenylsulfonylchloride as a brown powder (4.45 g, 97%): HPLC-MS (ESI): Calcd for C$_{13}$H$_6$Cl$_3$NO$_3$S [M+H]$^+$ 362, found: 362.

Example 1-1

N-(R-(+)-(1-azo-bicyclo[2.2.2]oct-3-yl)-5-cyano-2-(3,5-dichloro-phenoxy)-benzenesulfonamide

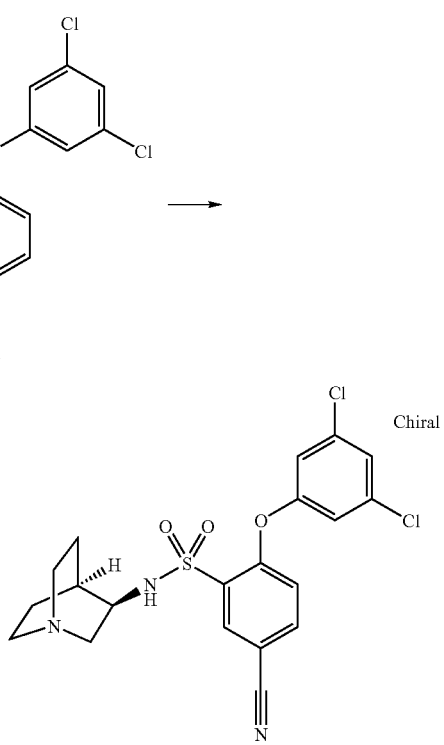

To a suspension of (R)-(+)-3-aminoquinuclidine 2HCl (2.87 g, 14.4 mmol) in dry CH$_2$Cl$_2$(25 ml) was added Et$_3$N (5.88 ml, 42.0 mmol). The mixture was stirred for 2 hours at room temperature followed by the addition of the solution of 5-cyano-2-(3,5-dichlorophenoxy)phenylsulfonyl-chloride (90%, 4.83 g, 12 mmol) in dry CH$_2$Cl$_2$ (10 ml) dropwise. After stirred for 5 hours at room temperature, CH$_2$Cl$_2$ (160 mL) was added and the mixture was washed with water, sat. Na$_2$CO$_3$ aq., brine and dried over MgSO$_4$. The solvent was evaporated, and the product was recrystallized from the mixture of EtOAc and hexane to give N-(R)-(+)-(1-aza-bicyclo[2.2.2]oct-3-yl)-5-cyano-2-(3,5-dichloro-phenoxy)-benzenesulfonamide (4.30 g, 79.2%) as white solid.

$^1$H NMR(300 MHz, CDCl$_3$): 1.46-1.59 (2H, m), 1.68-1.72 (1H, m), 1.86-1.88 (2H, m), 2.69-2.99(6H, m), 3.20-3.28 (1H, m), 3.46-3.51(1H, m), 7.00 (1H, d, J=8.67 Hz), 7.04 (2H, s), 7.32 (1H, t, J=1.7 Hz), 7.79 (1H, dd, J=8.64, 2.07 Hz), 8.31 (1H, d, J=2.07 Hz); HPLC-MS (ESI): Calcd for C$_{20}$H$_{19}$C$_{12}$N$_3$O$_3$S [M+H]$^+$ 452, found: 452.

Molecular weight: 452.36

Melting point: 215-220° C. (decomp.)

Activity grade CCR3: A

Activity grade IC$_{50}$: A

Example 1-2

5-cyano-2-(3,5-dichloro-phenoxy)-N-(2-dimethylamino-ethyl)-N-[2-(2,5-dioxo-pyrrolidin-1-yl)-ethyl]-benzenesulfonamide (1) 5-cyano-2-(3,5-dichloro-phenoxy)-N-(2-dimethylamino-ethyl)-benzenesulfonamide

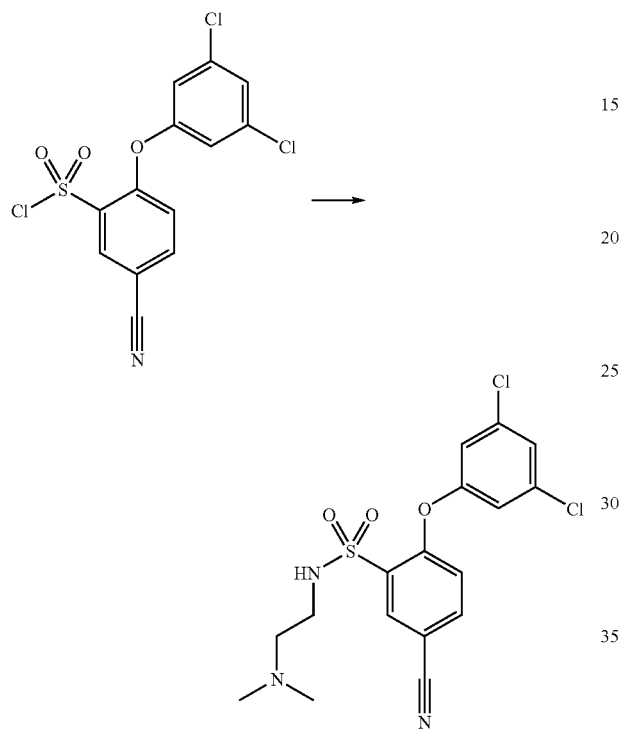

To a solution of N¹,N¹-dimethyl-ethane-1,2-diamine (74.0 mg, 0.84 mmol) and Et₃N in dry CH₂Cl₂ (3 ml) was added the solution of 5-cyano-2-(3,5-dichlorophenoxy)phenylsulfonylchloride (90%, 282 mg, 0.7 mmol) in dry CH₂Cl₂ (6 ml) dropwise. The resulting solution was stirred at room temperature for 1 hour. CH₂Cl₂ (60 ml) was added and the mixture was washed with water, brine, and dried over MgSO₄. The solvent was evaporated, and the residue was purified by column chromatography (CH₂Cl₂/CH₃OH=10:1) to give 5-cyano-2-(3,5-dichloro-phenoxy)-N-(2-dimethylamino-ethyl)-benzene-sulfonamide as white solid (220 mg, 75.9%): HPLC-MS (ESI): Calcd for $C_{19}H_{21}Cl_2N_3O_4S$ [M+H]⁺ 414, Found: 414

(2) 1-(2-bromo-ethyl)-pyrrolidine-2,5-dione

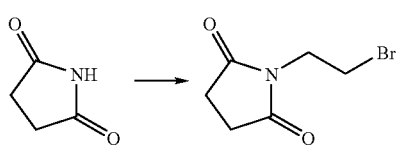

To a mixture of dihydro-furan-2,5-dione (396 mg, 4.00 mmol) and 1,2-dibromo-ethane (1.50 g, 8.00 mmol) in CH₃CN (20 ml) was added K₂CO₃ (829 mg, 6.00 mmol) at room temperature. The mixture was stirred at reflux overnight and the solvent was evaporated. The mixture was diluted with EtOAc (150 mL), washed with water, sat. Na₂CO₃aq., brine, and dried over MgSO₄. The solvent was evaporated to give 1-(2-bromo-ethyl)-pyrrolidine-2,5-dione that was used for next step without further purification (580 mg, 70.4%).

(3) 5-cyano-2-(3,5-dichloro-phenoxy)-N-(2-dimethylamino-ethyl)-N-[2-(2,5-dioxo-pyrrolidin-1-yl)-ethyl]-benzenesulfonamide

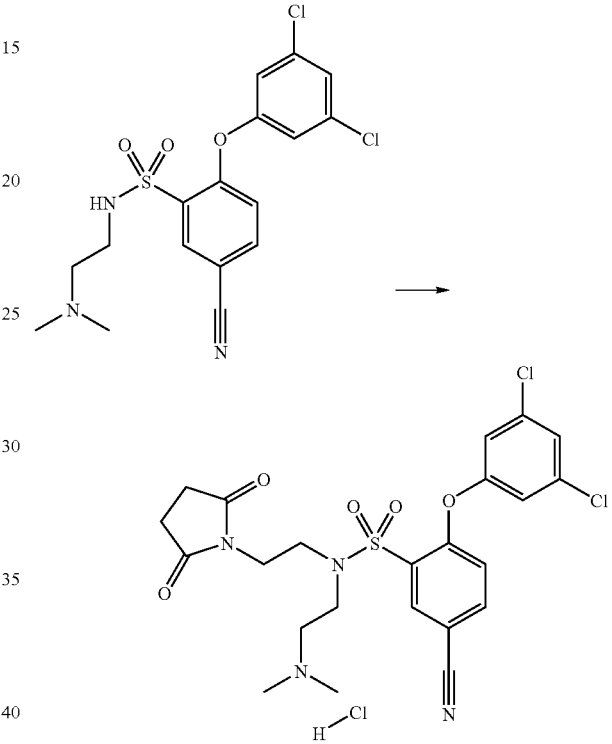

To a solution of 5-cyano-2-(3,5-dichloro-phenoxy)-N-(2-dimethylamino-ethyl)-benzene-sulfonamide (41.4 mg, 0.1 mmol) in dry DMF (2 ml) was added 1-(2-bromo-ethyl)-pyrrolidine-2,5-dione (30.9 mg, 0.15 mmol) and NaH (60%, 6.00 mg, 0.15 mmol). The mixture was stirred for 8 hours at 90° C. After cooled to room temperature, the solvent was evaporated. The mixture was diluted with EtOAc (60 ml), washed with brine, and dried over MgSO₄. The solvent was evaporated and the residue was purified by preparative TLC (CH₂Cl₂/CH₃OH=20/1) to give 5-cyano-2-(3,5-dichloro-phenoxy)-N-(2-dimethylamino-ethyl)-N-[2-(2,5-dioxo-pyrrolidin-1-yl)-ethyl]-benzenesulfonamide (44 mg, 81.6%) and the free base was converted into HCl salt by 4N HCl in dioxane.

¹H NMR(300 MHz, CDCl₃): δ 2.76 (4H, s), 2.85 (6H, s), 3.56 (4H, br, s), 3.74-3.80(2H, m), 3.94 (2H, br, s), 7.01 (1H, d, J=8.64 Hz), 7.09 (2H, s), 7.33 (1H, s), 7.81 (1H, d, J=8.64 Hz), 8.21 (1H, s); HPLC-MS (ESI): Calcd for $C_{23}H_{24}Cl_2N_4O_5S·HCl$ [M+H]⁺ 539, found: 539.

Molecular weight: 575.90

Melting point:

Activity grade CCR3: A

Activity grade IC₅₀: A

Example 1-3

4-(3,5-dichloro-phenoxy)-3-[(3S)-(1H-indol-3-ylmethyl)-piperazine-1-sulronyl]-benzonitrile (1) [(2S)-benzyloxycarbonylamino-3-(1H-indol-3-yl)-propionylamino]-acetic acid ethyl ester

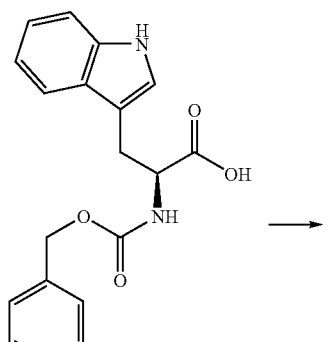

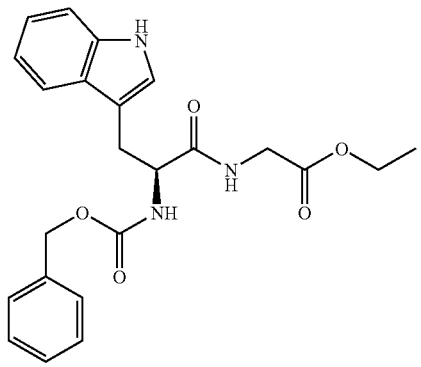

To a mixture of (2S)-benzyloxycarbonylamino-3-(1H-indol-3-yl)-propionic acid (4.16 g, 12.3 mmol), 1-ethyl-3-(3-dimethylaminopropyl) carbodiimide hydrogen chloride (2.83 g, 14.8 mmol), 1-hydroxybenzotriazole (1.99 g, 14.8 mmol) and Et$_3$N (5.14 ml, 36.9 mmol) in dry THF (20 ml) was added amino-acetic acid ethyl ester hydrogen chloride (1.72 g, 12.3 mmol) portionwise. The reaction mixture was stirred for 3 days at room temperature. The organic solvent was evaporated in vacuo, and the residue was diluted with EtOAc. The organic layer was washed with 0.5N HCl, saturated NaHCO$_3$aq., brine, and dried over MgSO$_4$. The organic layer was concentrated to give [(2S)-benzyloxycarbonylamino-3-(1H-indol-3-yl)-propionylamino]-acetic acid ethyl ester (5.10 g, 97.9%) as yellow sticky oil: HPLC-MS (ESI): Calcd for C$_{23}$H$_{25}$N$_3$O$_5$[M+H]$^+$ 424, found: 424.

(2) [(2S)-amino-3-(1H-indol-3-yl)-propionylamino]-acetic acid ethyl ester

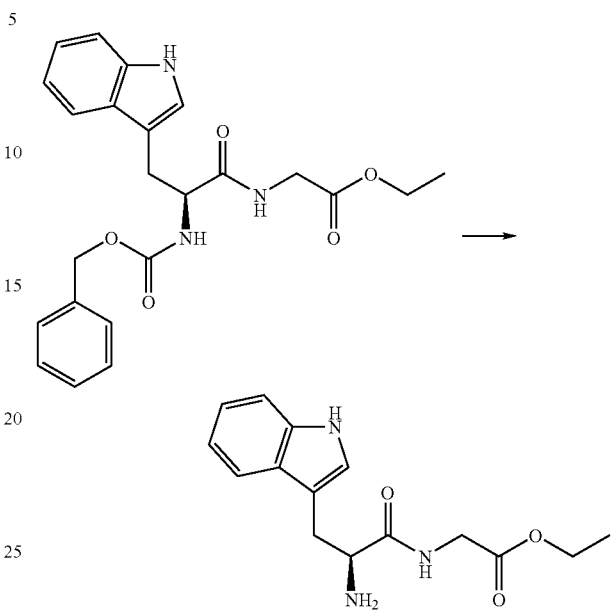

To a suspension of 10% Pd/C (0.50 g) in dry MeOH (70 ml) was added a solution of [(2S)-benzyloxycarbonylamino-3-(1H-indol-3-yl)-propionylamino]-acetic acid ethyl ester (5.10 g, 17.6 mmol) in dry MeOH (30 ml). The reaction mixture was stirred under 1 atm of H$_2$ in hydrogenator for 1 day at room temperature. After removing all particle with celite pad, the filtrate was concentrated in vacuo to give [(2S)-amino-3-(1H-indol-3-yl)-propionylamino]-acetic acid ethyl ester (3.26 g, 91.6%) as an oil: HPLC-MS (ESI): Calcd for C$_{15}$H$_{19}$N$_3$O$_3$[M+H]$^+$ 290, found: 290.

(3) (3S)-(1H-indol-3-ylmethyl)-piperazine-2,5-dione

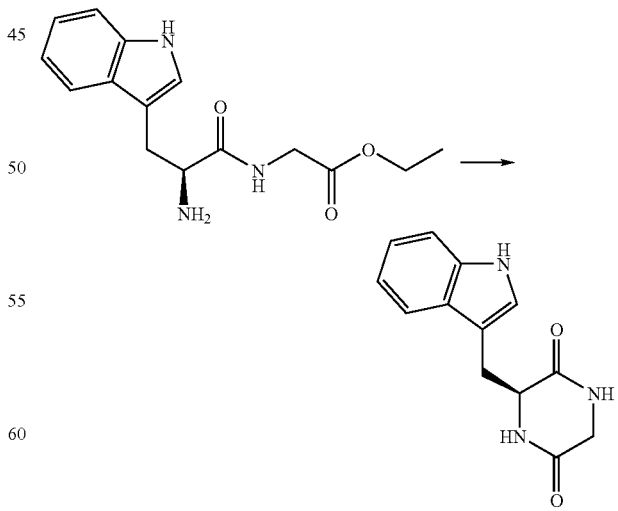

The solution of [(2S)-amino-3-(1H-indol-3-yl)-propionylamino]-acetic acid ethyl ester (3.25 g, 11.2 mmol) and Et$_3$N in dry MeOH was heated to reflux overnight. The resulting white precipitate was collected and dried to give (3S)-(1H-indol-3-ylmethyl)-piperazine-2,5-dione (1.80 g, 65.9%): HPLC-MS (ESI): Calcd for $C_{13}H_{13}N_3O_2[M+H]^+$ 244, found: 244.

(4) 3-(piperazin-(2S)-ylmethyl)-1H-indole

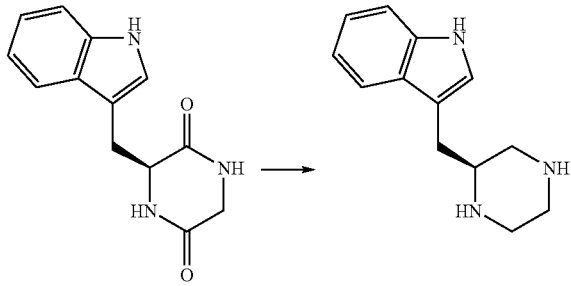

To a suspension of lithium aluminum hydride (0.19 g, 5.08 mmol) in dry THF (10 ml) was added the solution (3S)-(1H-indol-3-ylmethyl)-piperazine-2,5-dione (0.30 g, 1.23 mmol) in THF (10 ml) dropwise. The reaction mixture was stirred at 75° C. overnight, cooled to room temperature. 0.19 ml of water, 0.19 mL of 4N NaOH aq., and 0.58 ml of water were successively added to the mixture at 0° C. The resulting white precipitate was filtered off with celite pad, and the filtrate was concentrated in vacuo to give 3-(piperazin-(2S)-ylmethyl)-1H-indole (0.26 g, quant.) as a yellow oil: HPLC-MS (ESI): Calcd for $C_{13}H_{17}N_3[M+H]^+$ 216, found: 216.

(5) 4-(3,5-dichloro-phenoxy)-3-[(3S)-(1H-indol-3-ylmethyl)-piperazine-1-sulfonyl]-benzonitrile

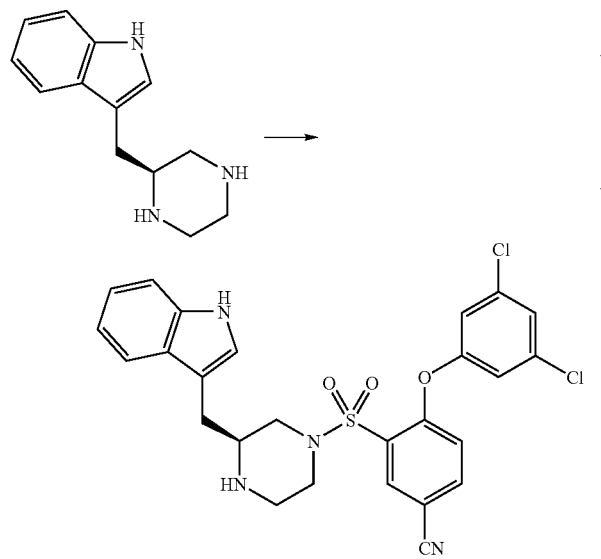

To a solution of 3-(piperazin-(2S)-ylmethyl)-1H-indole (33.0 mg, 0.15 mmol) and di-isopropyl-ethyl amine (0.08 mL, 0.46 mmol) in dry THF (2 mL) was added 5-cyano-2-(3,5-dichloro-phenoxy)-benzene-sulfonyl chloride (50.0 mg, 0.14 mmol) in portions. The reaction mixture was stirred for 2 hours at room temperature. The solvent was evaporated in vacuo. The residue was purified by preparative TLC ($CH_2Cl_2$/MeOH=10/1) twice to give 4-(3,5-dichloro-phenoxy)-3-[(3S)-(1H-indol-3-ylmethyl)-piperazine-1-sulfonyl]-benzonitrile (6.20 mg, 7.5%) as a white solid.

$^1$H NMR (300 MHz, $CDCl_3$) δ 2.56-3.07 (7H, m), 3.71-3.75 (1H, d, J=10.9 Hz), 3.83-3.86 (1H, d, J=11.1 Hz), 6.98 (2H, d, J=1.7 Hz), 7.04-7.05 (1H, d, J=2.3 Hz), 7.10-7.15 (1H, t, J=7.0 Hz), 7.20-7.25 (1H, t, J=7.0 Hz), 7.28-7.29 (1H, t, J=1.9 Hz), 7.37-7.40 (1H, d, J=7.9 Hz), 7.55-7.58 (1H, d, J=7.5 Hz), 7.75-7.78 (1H, dd, J=2.1, 8.7 Hz), 8.09 (1H, br), 8.28-8.29 (1H, d, J=2.1 Hz); HPLC-MS (ESI): Calcd for $C_2H_{22}Cl_2N_4O_3S[M+H]^+$ 541, found: 541.

Molecular weight: 541.46
Melting point: 128-129° C.
Activity grade CCR3: A
Activity grade $IC_{50}$: A Example 1-4

4-(3,5-dichlorophenoxy)-3-{[2-(1H-1,2,4-triazol-1-ylmethyl)-1-piperazinyl]sulfonyl}benzo-nitrile hydrochloride (1) 1,4-dibenzyl-piperazine-2-carboxylic acid methyl ester

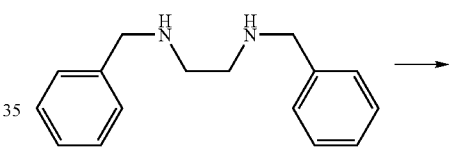

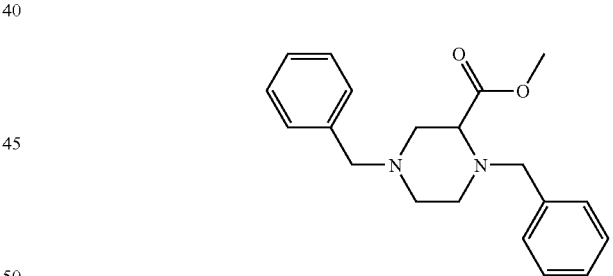

To the preheated solution (50° C.) of 2,3-dibromo-propionic acid methyl ester in toluene (40 ml) and $Et_3N$ (5.80 ml, 41.6 mmol), was added N,N'-dibenzyl-ethane-1,2-diamine (4.90 ml, 20.8 mmol) dropwise. Resulting white slurry was heated to reflux to a clear solution and the solution was stirred at reflux overnight. After cooled to room temperature, the reaction mixture was extracted with 2N HCl (ca. 500 ml) and the extract was neutralized with 4N NaOH. The aqueous layer was extracted with EtOAc three times. The organic layer was washed with brine, dried over $MgSO_4$, and concentrated to give 1,4-dibenzyl-piperazine-2-carboxylic acid methyl ester (5.73 g, 84.8%) as a colorless oil: HPLC-MS (ESI): Calcd for $C_{20}H_{24}N_2O_2[M+H]^+$ 325, found: 325.

(2) (1,4-dibenzyl-piperazin-2-yl)-methanol

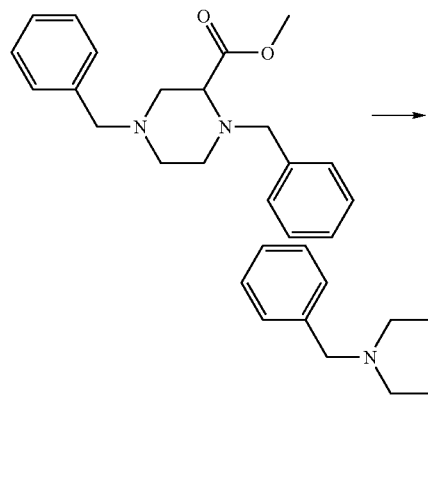

To the suspension of lithium aluminum hydride (1.54 g, 40.6 mmol) was added 1,4-dibenzyl-piperazine-2-carboxylic acid methyl ester (3.00 g, 9.25 mmol) portionwise at room temperature. The reaction mixture was stirred at reflux for 3 hours. After cooled to 0° C., 1.5 ml of water, 1.5 ml of 4N NaOH aq., and 4.5 ml of water was added successively. The mixture was stirred for 1 hour, and the white precipitate was filtered off with celite pad. The filtrate was concentrated in vacuo to give (1,4-dibenzyl-piperazin-2-yl)-methanol (2.74 g, quant.) as a yellow oil: HPLC-MS (ESI): Calcd for $C_{19}H_{24}N_2O[M+H]^+$ 297, found: 297.

(3) 1,4-dibenzyl-2-chloromethyl-piperazine

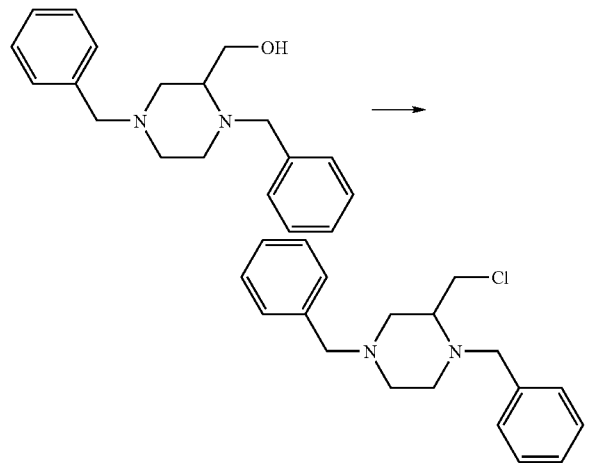

To the solution of thionyl chloride (1.63 ml, 22.4 mmol) in $CCl_4$ (30 ml) was added the solution of (1,4-dibenzylpiperazin-2-yl)-methanol (2.74 g, 9.25 mmol) in $CCl_4$ dropwise in 10 minutes. The produced suspension was stirred for 2 hours at 77° C. After cooled to room temperature, 20 ml of ice water was added and the aqueous layer was separated from the organic solvent. The PH of aqueous layer was adjusted to 12 with 4N NaOH aq., and extracted with $CHCl_3$ three times. The combined organic layer was dried over $MgSO_4$, and concentrated to give brownish oil which was purified by column chromatography on silica gel ($CH_2Cl_2$/MeOH=30/1) to give 1,4-dibenzyl-2-chloromethyl-piperazine in crude form (3.08 g, 95%, ca. 90% purity from HPLC analysis). The compound was used for next reaction without further purification: HPLC-MS (ESI): Calcd for $C_{19}H_{23}ClN_2[M+H]^+$ 315, found: 315.

(4) 1,4-dibenzyl-2-(1H-1,2,4-triazol-1-ylmethyl)piperazine

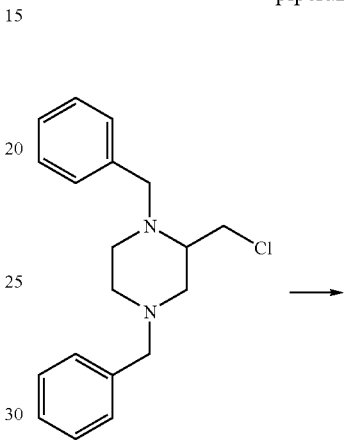

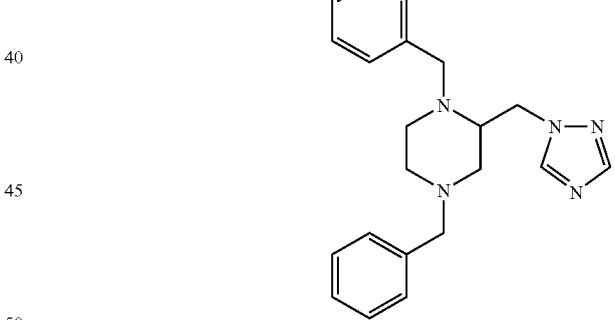

To a solution of 1,2,4-triazole (48.3 mg, 0.70 mmol) in DMF (2 ml) was added NaH (18.3 mg, 0.76 mmol). After 10 minutes stirring, 1,4-dibenzyl-2-(chloromethyl)piperazine (200 mg, 0.64 mmol) and KI (156 mg, 0.70 mmol) were added to the mixture. The mixture was stirred at 60° C. overnight. The mixture was diluted with EtOAc and washed with water and brine. The organic layer was dried over $MgSO_4$, filtered and concentrated in vacuo. The resulting residue was purified by column chromatography on NH-silica gel (Hex/AcOEt=¼) to give 1,4-dibenzyl-2-(1H-1,2,4- triazol-1-ylmethyl)piperazine (220.0 mg, 99.7%): HPLC-MS (ESI): Calcd for $C_{21}H_{25}N_5$ [M+H]$^+$ 348, found: 348.

(5) 2-(1H-1,2,4-triazol-1-ylmethyl)piperazine dihydrochloride

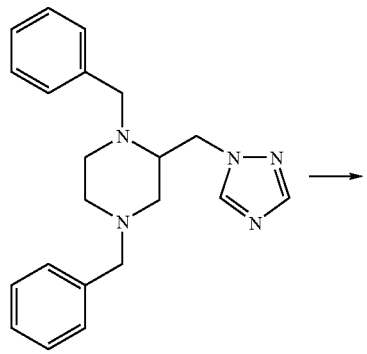

To a solution of 1,4-dibenzyl-2-(1H-1,2,4-triazol-1-ylmethyl)piperazine (206 mg, 0.59 mmol) in MeOH (3.0 ml) was added a few drops of 4N HCl in 1,4-dioxane and 20% wet Pd(OH)$_2$ (100 mg). The mixture was stirred overnight under H$_2$ atmosphere with a balloon. The catalyst was filtered off through Celite pad and the filtrate was concentrated in vacuo to give 2-(1H-1,2,4-triazol-1-ylmethyl)piperazine dihydrochloride (122.9 mg, 86.3%): HPLC-MS(ESI): Calcd for $C_7H_{13}N_5$ [M+H]$^+$ 168, found: 168.

(6) tert-butyl 3-(1H-1,2,4-triazol-1-ylmethyl)-1-piperazinecarboxylate

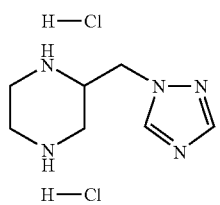

To a suspension of 2-(1H-1,2,4-triazol-1-ylmethyl)piperazine dihydrochloride (104 mg, 0.39 mmol) and Et$_3$N (157.7 mg, 1.56 mmol) in CH$_2$Cl$_2$ (3 ml) was added [{[(tert-butoxycarbonyl)oxy]amino}(cyano)methyl]benzene (106.5 mg, 0.43 mmol). The mixture was stirred for 2 hours at room temperature. The solvent was evaporated in vacuo, and the residue was purified by column chromatography on silica gel (MeOH/CHCl$_3$=1/50-1/10) to give tert-butyl 3-(1H-1,2,4-triazol-1-ylmethyl)-1-piperazinecarboxylate (50.9 mg, 48.9%): HPLC-MS (ESI): Calcd for C, H$_{20}$N$_6$O$_2$ [M+H]$^+$ 268, found: 268.

(7) tert-butyl 4-{[5-cyano-2-(3,5-dichlorophenoxy)phenyl]sulfonyl}-3-(1H-1,2,4-triazol-1-ylmethyl)-1-piperazinecarboxylate

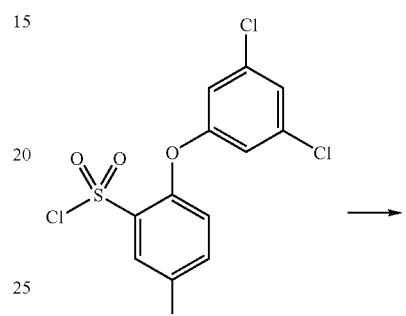

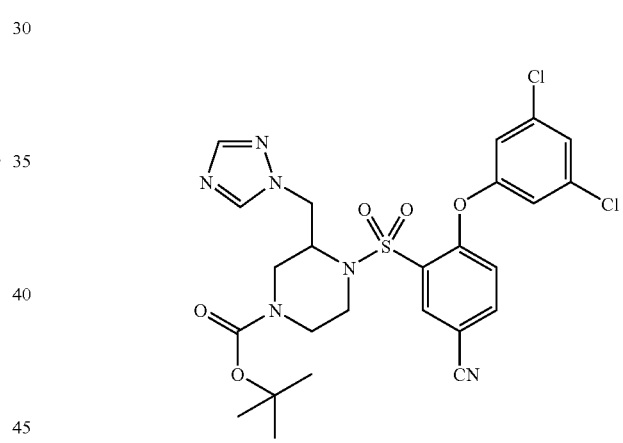

To a solution of tert-butyl 3-(1H-1,2,4-triazol-1-ylmethyl)-1-piperazinecarboxylate (29.5 mg, 0.11 mmol) and di-isopropyl-ethyl amine (28.5 mg, 0.22 mmol) in THF (2 ml) was added 5-cyano-2-(3,5-dichlorophenoxy)benzenesulfonyl chloride (40.0 mg, 0.11 mmol). The mixture was stirred at 50° C. overnight. The solvent was removed and the residue was diluted with CHCl$_3$, washed with sat. NaHCO$_3$ aq. and brine. The organic layer was dried over MgSO$_4$. The solvent was evaporated in vacuo, and the resulting residue was purified by prep. TLC (MeOH/CHCl3=1/10) to give tert-butyl 4-{[5-cyano-2-(3,5-dichlorophenoxy)phenyl]sulfonyl}-3-(1H-1,2,4-triazol-1-yl methyl)-1-piperazine-carboxylate (42.5 mg, 64.9%): HPLC-MS (ESI): Calcd for $C_{25}H_{26}Cl_2N_6O_5S$ [M+H]$^+$ 593, found: 593.

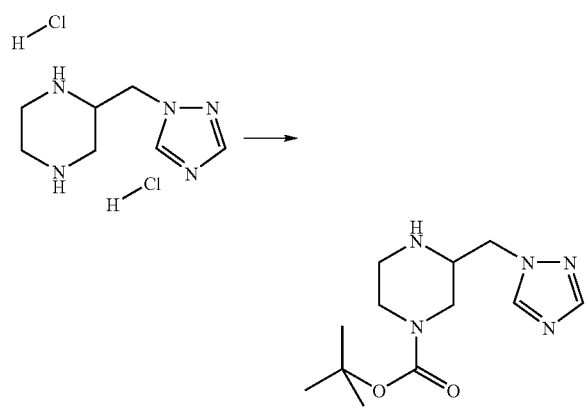

(8) 4-(3,5-dichlorophenoxy)-3-{[2-1H-1,2,4-triazol-1-ylmethyl)-1-piperazinyl]-sulfonyl}benzonitrile hydrochloride

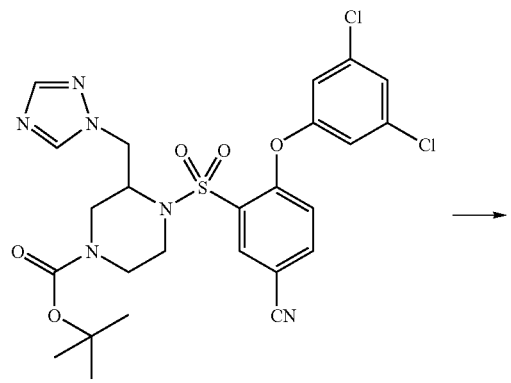

To a solution of tert-butyl 4-{[5-cyano-2-(3,5-dichlorophenoxy) phenyl]sulfonyl}-3-(1H-1,2,4-triazol-1-ylmethyl)-1-piperazinecarboxylate (37 mg, 0.06 mmol) in $CH_2Cl_2$ (1 ml) was added 4N HCl in 1,4-dioxane (1 ml). The mixture was stirred for 2 hours at room temperature. The solvent was evaporated in vacuo, the residue was triturated with $Et_2O$ and the white solid was collected by filtration to give 4-(3,5-dichlorophenoxy)-3-{[2-(1H-1,2,4-triazol-1-ylmethyl)-1-piperazinyl]sulfonyl}benzonitrile hydrochloride (28.5 mg, 86.3%).

$^1$H NMR(500 MHz, DMSO-$d_6$): 2.30-3.37 (1H, m), 3.71 (1H, t, J=12.9 Hz), 4.01 (2H, d, J=14.2 Hz), 4.56 (1H, dd, J=14.2, 5.4 Hz), 4.60-4.63 (1H, m), 4.82 (1H, dd, J=13.9, 9.5 Hz), 7.21 (1H, d, J=8.5 Hz), 7.40 (2H, d, J=1.6 Hz), 7.59 (1H, t, J=3.5, 1.6 Hz), 7.68 (1H, s), 8.05 (1H, d, J=2.2 Hz), 8.07 (1H, s), 8.59 (1H, s), 9.51 (1H, br, s), 9.58 (1H, br, s); HPLC-MS (ESI): Calcd for $C_{25}H_{26}Cl_2N_6O_5S$ [M+H]$^+$ 494, found: 494.

Molecular weight: 529.84
Melting point: 177° C. (decomp.);
Activity grade CCR3: A
Activity grade IC$_{50}$: A The compounds in Example 1-5 to −47 as shown in Table I were synthesized similar procedure as described in Example 1-1 to 1-4 above or conventional reactions.

TABLE 1

| Ex No | Structure | Mol weight | MASS | MP (° C.) | CCR3 | IC50 |
|---|---|---|---|---|---|---|
| 1-5 | 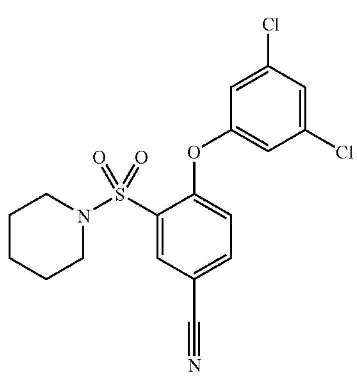 | 411.31 | 411 | 171-172 | C | C |

TABLE 1-continued

| Ex No | Structure | Mol weight | MASS | MP (° C.) | CCR3 | IC50 |
|---|---|---|---|---|---|---|
| 1-6 | 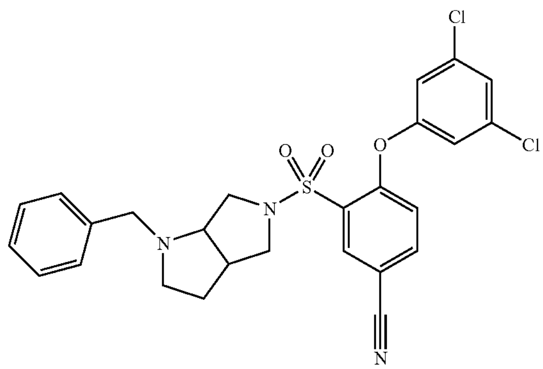 | 528.46 | 528 | | A | A |
| 1-7 | 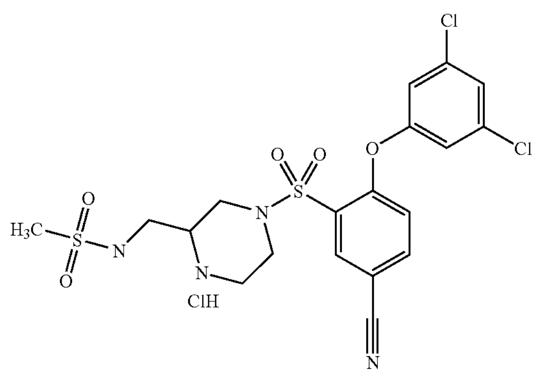 | 555.89 | 519 | 296 Z | A | A |
| 1-8 | 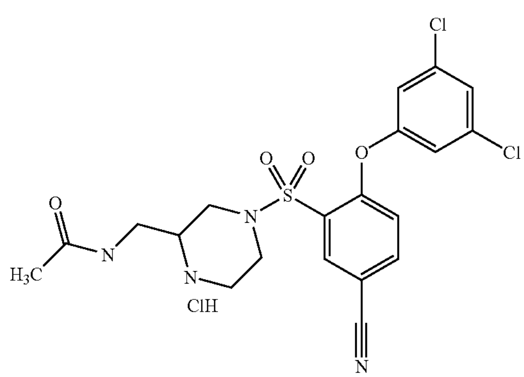 | 519.84 | 483 | >160 Z | A | A |
| 1-9 | 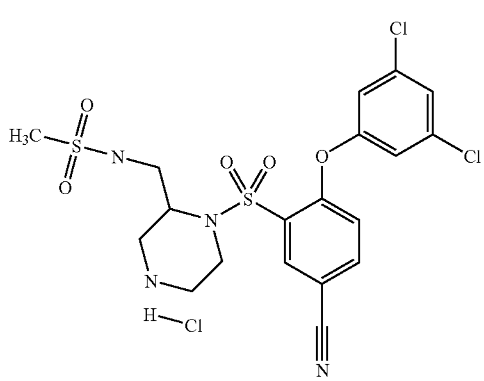 | 555.89 | 519 | 270 Z | A | A |

TABLE 1-continued

| Ex No | Structure | Mol weight | MASS | MP (° C.) | CCR3 | IC50 |
|---|---|---|---|---|---|---|
| 1-10 | 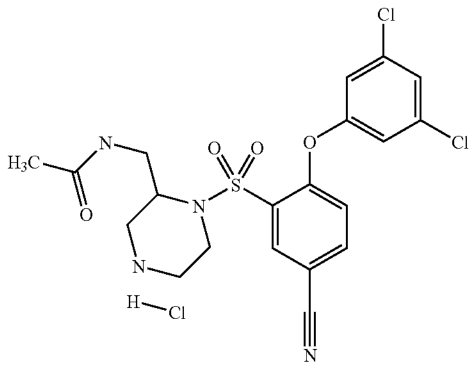 | 519.84 | 483 | >160 Z | A | A |
| 1-11 | 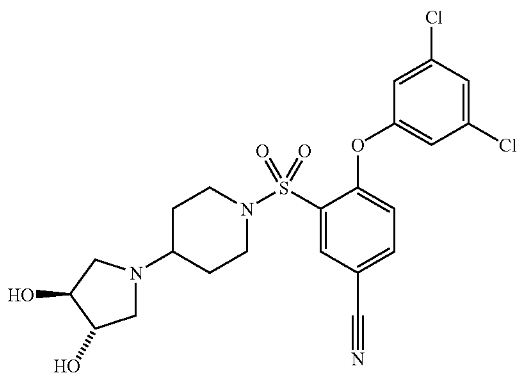 | 512.421 | 512 | 137-139 | B | A |
| 1-12 | 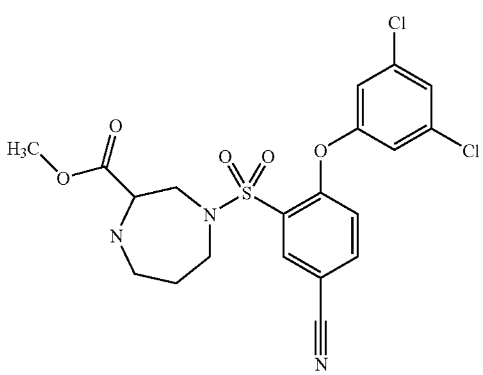 | 484.36 | 484 | | B | B |
| 1-13 | 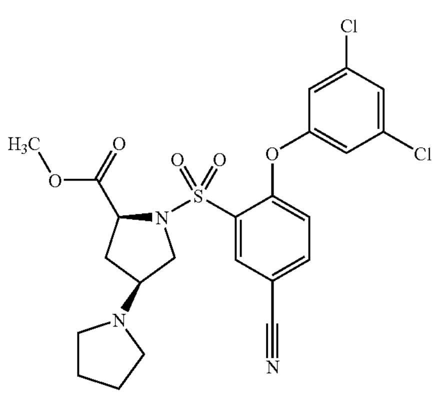 | 524.43 | 524 | | B | A |

TABLE 1-continued

| Ex No | Structure | Mol weight | MASS | MP (° C.) | CCR3 | IC50 |
|---|---|---|---|---|---|---|
| 1-14 | 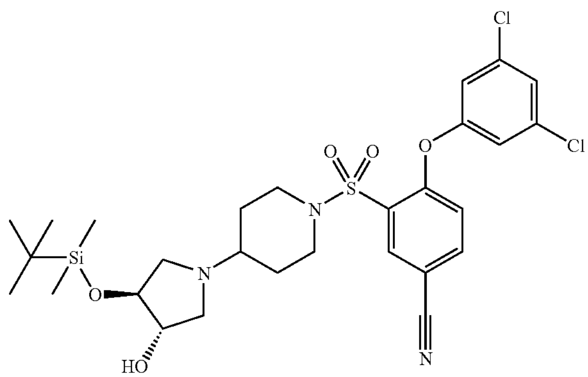 | 626.68 | 626 | | | B |
| 1-15 | 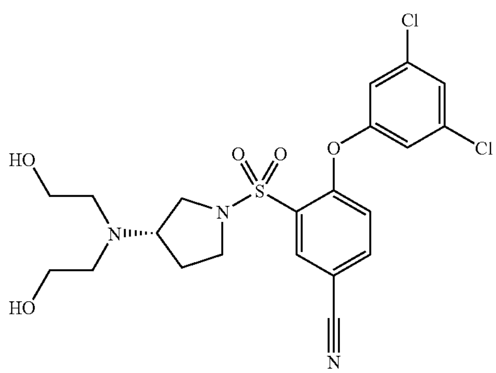 | 500.4 | 500 | 153-154 | | B |
| 1-16 | 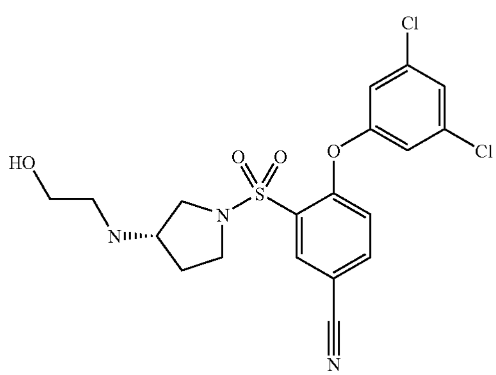 | 456.35 | 456 | 155-156 | A | A |
| 1-17 | 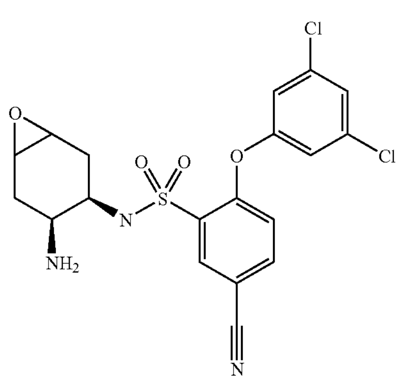 | 454.33 | 454 | 165-182 Z | | C |

TABLE 1-continued

| Ex No | Structure | Mol weight | MASS | MP (° C.) | CCR3 | IC50 |
|---|---|---|---|---|---|---|
| 1-18 | 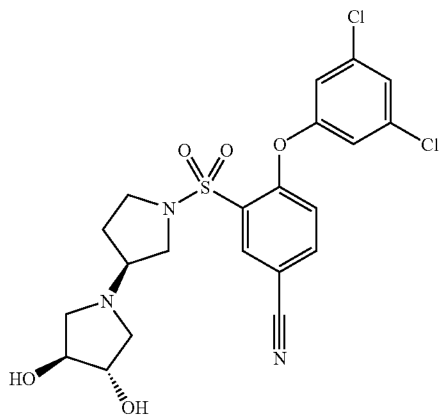 | 498.39 | 498 | | | B |
| 1-19 | 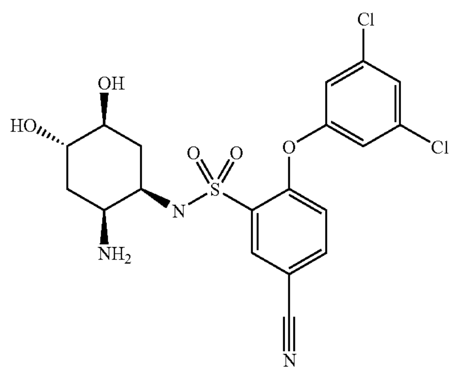 | 472.35 | 472 | | | C |
| 1-20 | 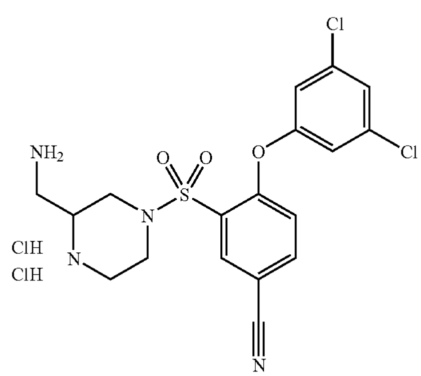 | 514.26 | 441 | 240-241 | | C |
| 1-21 | 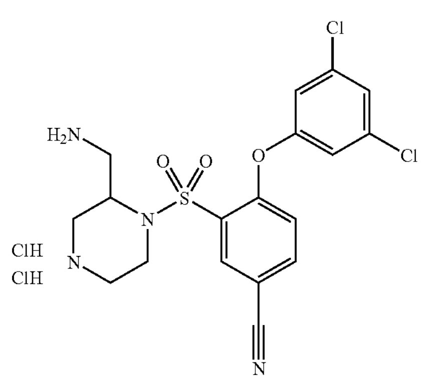 | 514.26 | 441 | 280-281 | A | A |

TABLE 1-continued

| Ex No | Structure | Mol weight | MASS | MP (° C.) | CCR3 | IC50 |
|---|---|---|---|---|---|---|
| 1-22 | 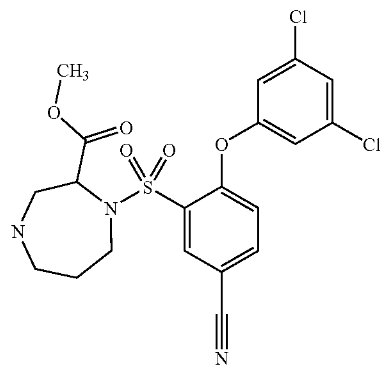 | 520.82 | 525(484 plus CH3CN) | 150 Z | A | A |
| 1-23 | 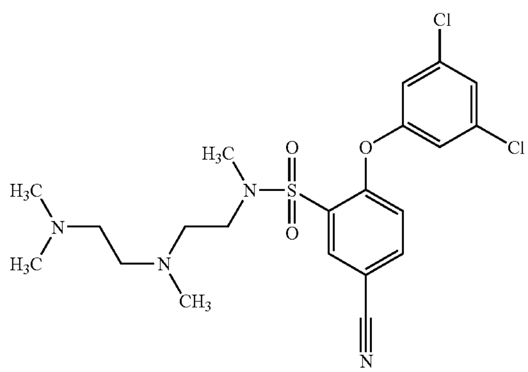 | 485.44 | 485 | | | B |
| 1-24 | 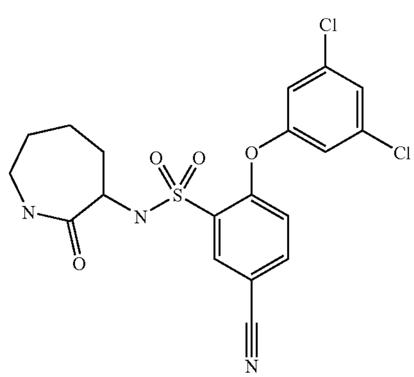 | 454.34 | 454 | 172-173 | | B |
| 1-25 | 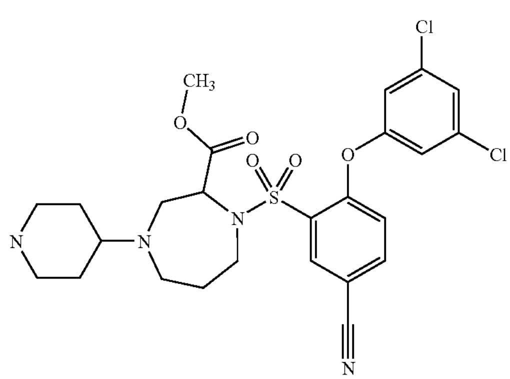 | 567.5 | 567 | >95 Z | | B |

TABLE 1-continued

| Ex No | Structure | Mol weight | MASS | MP (° C.) | CCR3 | IC50 |
| --- | --- | --- | --- | --- | --- | --- |
| 1-26 | 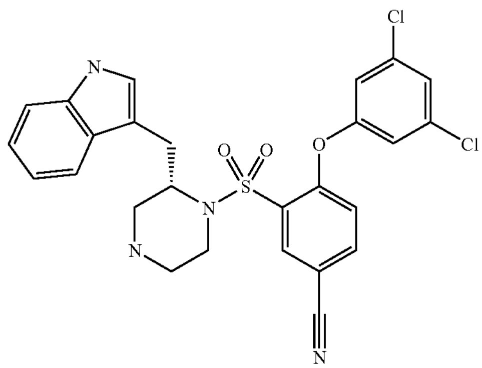 | 541.46 | 541 | 116-117 | A | A |
| 1-27 | 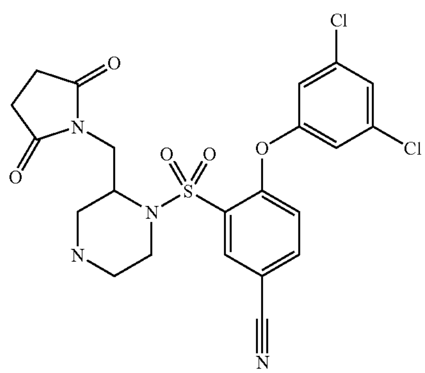 | 523.4 | 523 | | A | A |
| 1-28 | 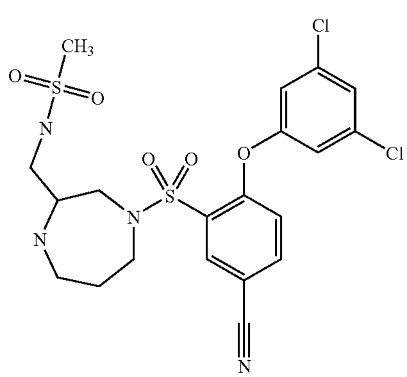 | 533.46 | 533 | 127 Z | A | A |
| 1-29 | 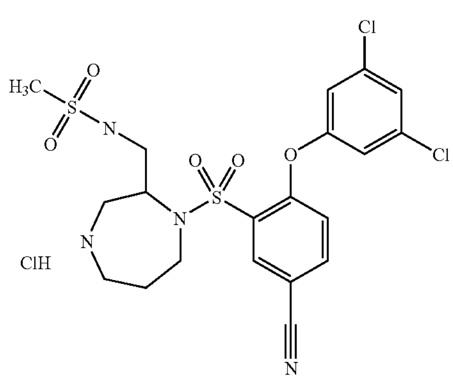 | 569.92 | 533 | 183-184 | A | A |

TABLE 1-continued

| Ex No | Structure | Mol weight | MASS | MP (° C.) | CCR3 | IC50 |
|---|---|---|---|---|---|---|
| 1-30 | 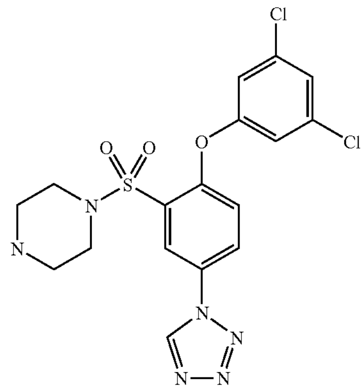 | 455.33 | 455 | >185 Z | | C |
| 1-31 | 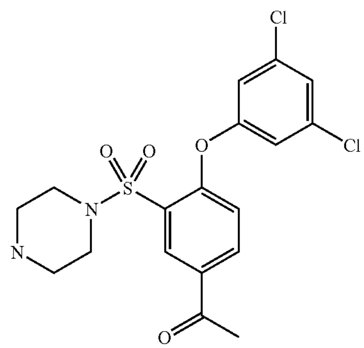 | 429.33 | 429 | 169-170 | A | A |
| 1-32 | 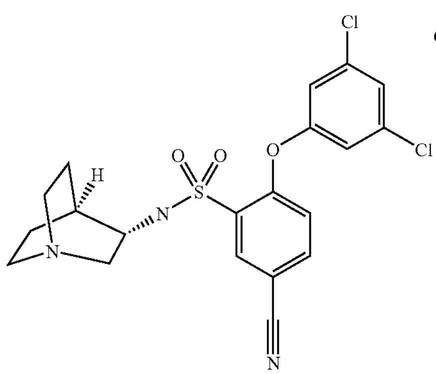 | 452.36 | 452 | | A | A |
| 1-33 | 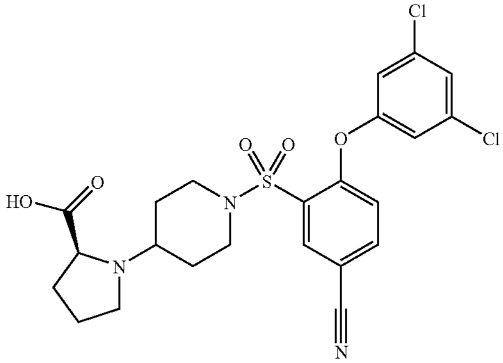 | 524.43 | 524 | 224-225 | A | B |

TABLE 1-continued

| Ex No | Structure | Mol weight | MASS | MP (° C.) | CCR3 | IC50 |
|---|---|---|---|---|---|---|
| 1-34 | 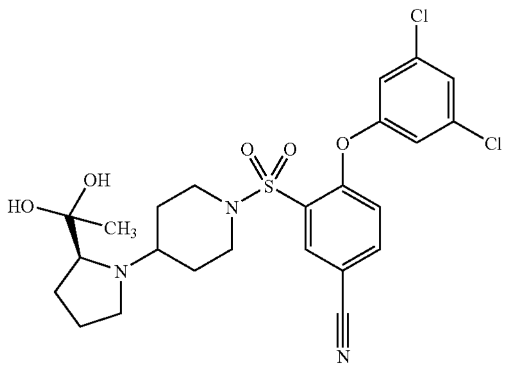 | 538.5 | 538 | 103 | A | A |
| 1-35 | 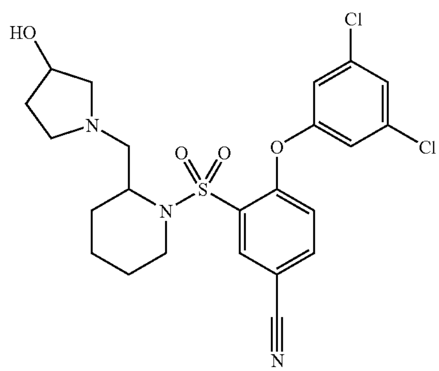 | 510.44 | 509 | | B | A |
| 1-36 | 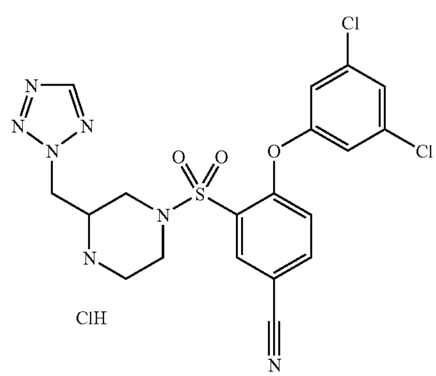 | 530.82 | 494 | 178 Z | A | A |
| 1-37 | 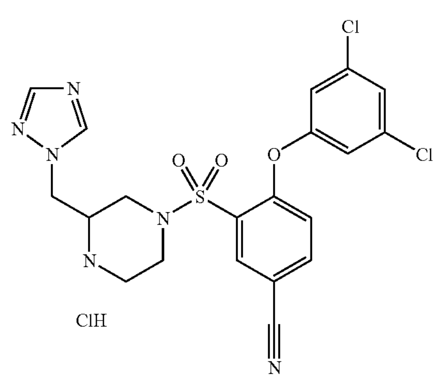 | 529.84 | 493 | 184-185 Z | A | A |

TABLE 1-continued

| Ex No | Structure | Mol weight | MASS | MP (° C.) | CCR3 | IC50 |
|---|---|---|---|---|---|---|
| 1-38 | 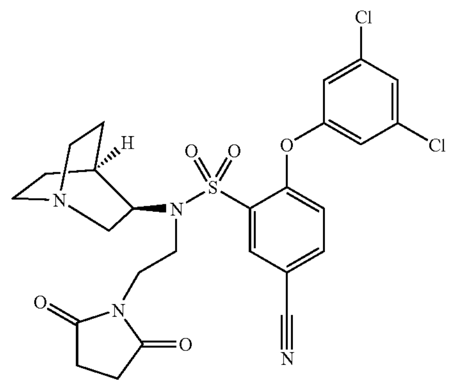 | 577.49 | 577 | | | C |
| 1-39 | 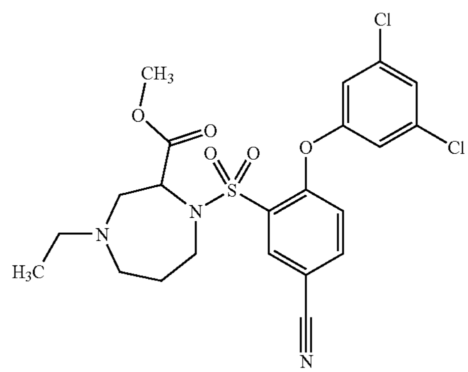 | 512.42 | 512 | | B | A |
| 1-40 | 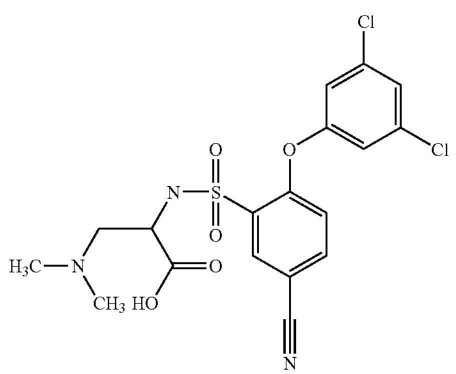 | 458.32 | 458 | 190 | | C |
| 1-41 | 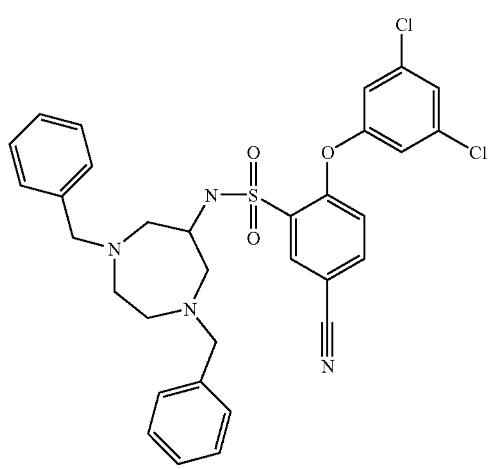 | 621.59 | 621 | | | C |

TABLE 1-continued

| Ex No | Structure | Mol weight | MASS | MP (° C.) | CCR3 | IC50 |
|---|---|---|---|---|---|---|
| 1-42 | 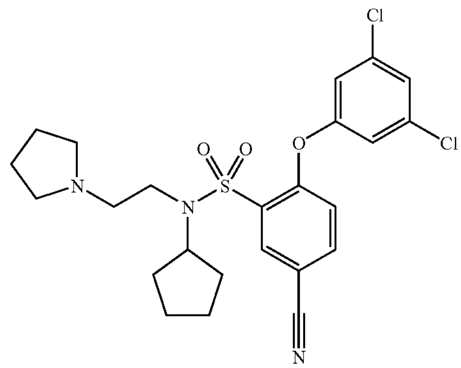 | 508.47 | 508 | | B | A |
| 1-43 | 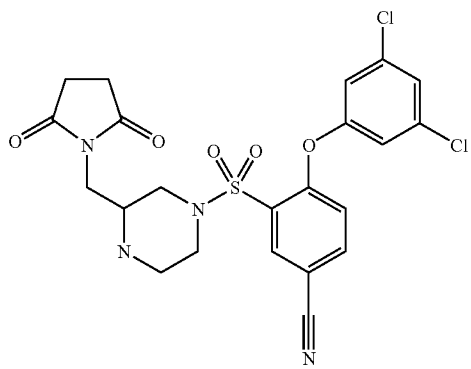 | 523.4 | 523 | 123-125 | A | A |
| 1-44 | 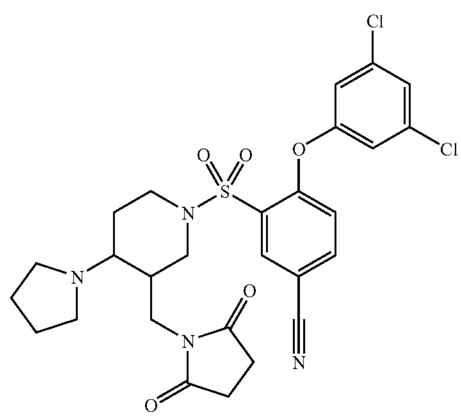 | 591.52 | 591 | 121 | A | A |
| 1-45 | 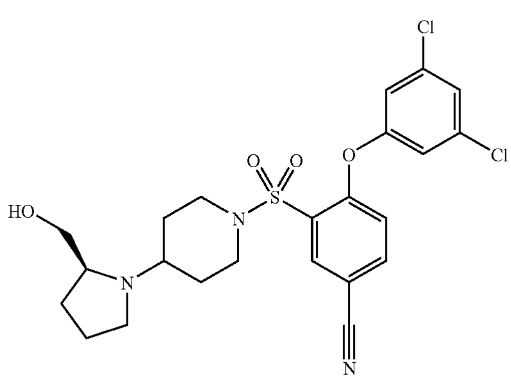 | 510.44 | 510 | 124 | A | A |

US 7,674,797 B2

TABLE 1-continued

| Ex No | Structure | Mol weight | MASS | MP (° C.) | CCR3 | IC50 |
|---|---|---|---|---|---|---|
| 1-46 | 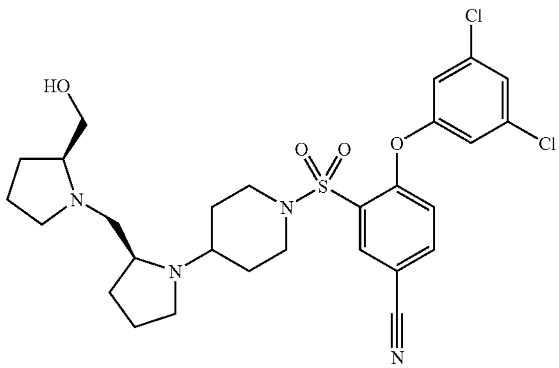 | 510.44 | 510 | 157 | A | A |
| 1-47 | 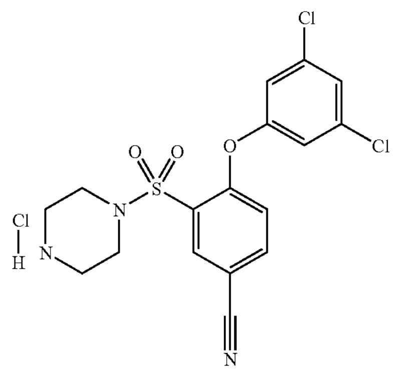 | 447.77 | 411 | 220-226 Z | C | C |

Z: Decomposed

Example 2-1

4-(3,5-Dichloro-phenoxy)-3-(piperidine-4-sulfonyl)-benzonitrile

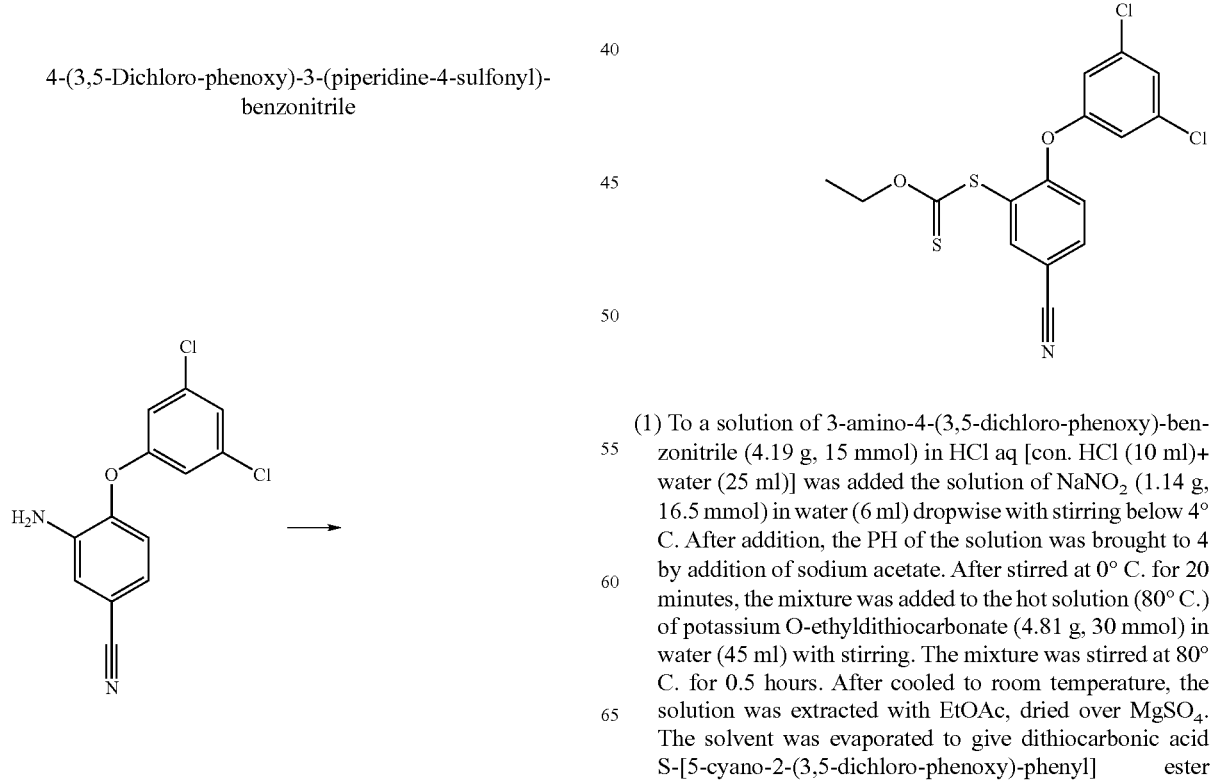

(1) To a solution of 3-amino-4-(3,5-dichloro-phenoxy)-benzonitrile (4.19 g, 15 mmol) in HCl aq [con. HCl (10 ml)+ water (25 ml)] was added the solution of NaNO$_2$ (1.14 g, 16.5 mmol) in water (6 ml) dropwise with stirring below 4° C. After addition, the PH of the solution was brought to 4 by addition of sodium acetate. After stirred at 0° C. for 20 minutes, the mixture was added to the hot solution (80° C.) of potassium O-ethyldithiocarbonate (4.81 g, 30 mmol) in water (45 ml) with stirring. The mixture was stirred at 80° C. for 0.5 hours. After cooled to room temperature, the solution was extracted with EtOAc, dried over MgSO$_4$. The solvent was evaporated to give dithiocarbonic acid S-[5-cyano-2-(3,5-dichloro-phenoxy)-phenyl] ester O-ethyl ester that was used for next reaction without further purification [5.50 g, 66.8% (70% purity)].

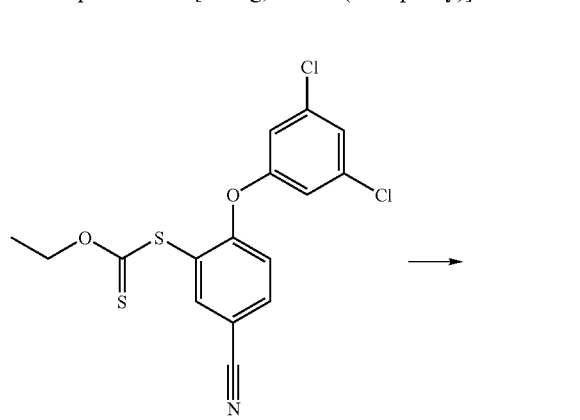

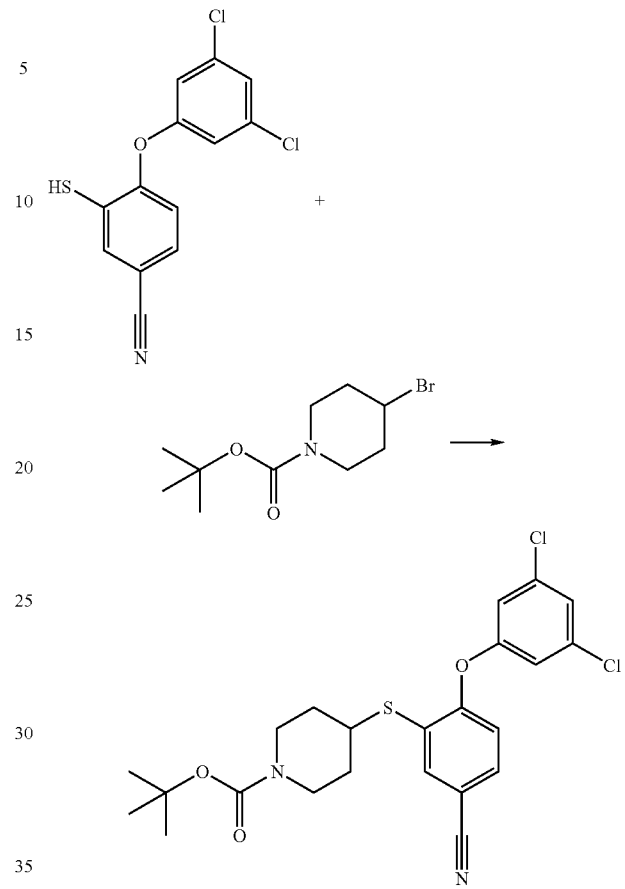

(2) The mixture of dithiocarbonic acid S-[5-cyano-2-(3,5-dichloro-phenoxy)-phenyl] ester O-ethyl ester [5.50 g, 10.2 mmol (70% purity)], KOH (3.37 g, 60.1 mmol) in ethanol (20 ml) was refluxed for 1 hour. After cooled to room temperature, the solvent was evaporated. 30 ml of ice water was added to the residue. The PH of the mixture was adjusted to 4 by addition of acetic acid. The mixture was extracted with EtOAc. The extract was washed with water, brine, dried over $MgSO_4$. The solvent was evaporated to give 4-(3,5-Dichloro-phenoxy)-3-mercapto-benzonitrile that was used for next reaction without purification [3.20 g, 75.5% (70% purity)].

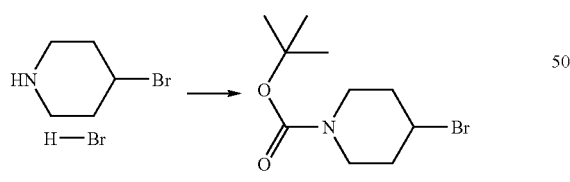

(3) To the suspension of 4-bromo-piperidine; hydrobromide (2.94 g, 12 mmol) in $CH_2Cl_2$ (30 ml) was added $NEt_3$ (3.04 g, 4.2 ml, 30 mmol) with stirring. Di-tert-butyl dicarbonate (3.14 g, 14.4 mmol) was added 10 min later. The mixture was stirred at room temperature for 3 hours, and diluted with $CH_2Cl_2$ (60 ml). The mixture was washed with 0.2 N HCl aq., 5% $NaHCO_3$ aq., brine, dried over $MgSO_4$. The solvent was evaporated to give 4-bromo-piperidine-1-carboxylic acid tert-butyl as colorless liquid that was used for the next step without further purification [2.60 g, 69.5% (70% purity)].

(4) The mixture of 4-(3,5-dichloro-phenoxy)-3-mercapto-benzonitrile ester [338 mg, 0.8 mmol, (70% purity)], 4-bromo-piperidine-1-carboxylic acid tert-butyl [362 mg, 0.96 mmol(70% purity)], and $K_2CO_3$ (552 mg, 4 mmol) in dry DMF(8 ml) was stirred at 95° C. overnight. The solvent was evaporated, and the residue was diluted with EtOAc (100 ml). The mixture was washed with brine, and the organic layer was dried over $MgSO_4$. The solvent was evaporated to give 4-[5-cyano-2-(3,5-dichloro-phenoxy)-phenylsulfanyl]-piperidine-1-carboxylic acid tert-butyl ester that was used for the next reaction without any purification [360 mg, 56.3% (60% purity)].

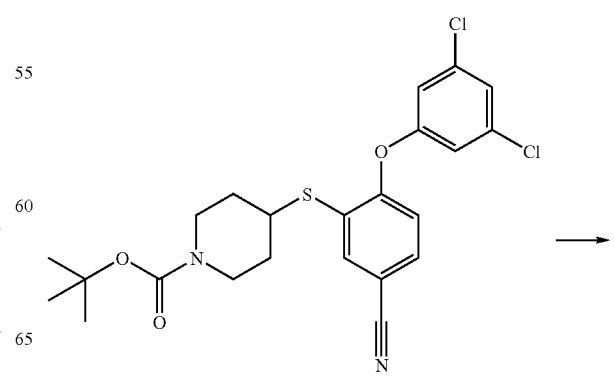

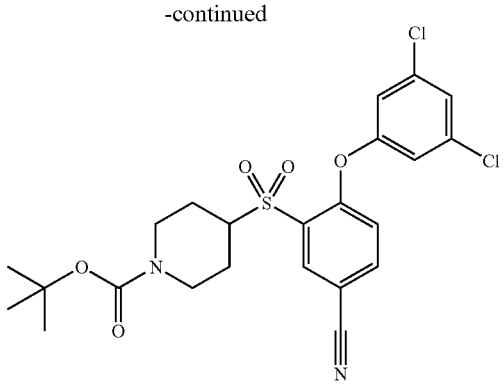

(5) To a solution of 1-[5-cyano-2-(3,5-dichloro-phenoxy)-phenylsulfanyl]-piperidine-1-carboxylic acid tert-butyl ester [320 mg, 0.4 mmol (60 purity)] in the mixture of CCl$_4$ (6 ml) and CH$_3$CN (6 ml) was added the solution of NaIO$_4$ (599 mg, 2.80 mmol) and RuCl$_3$ (41.5 mg, 0.2 mmol) in water (12 ml). The mixture was stirred at room temperature for 4 hours, and the solvent was evaporated. The residue was diluted with EtOAc (100 ml). The mixture was washed with water, brine, and dried over MgSO$_4$. The solvent was evaporated and the crude product was purified by preparative TLC (EtOAC/Hexane=1:1) to give 4-[5-cyano-2-(3,5-dichloro-phenoxy)-benzene-sulfonyl]-piperidine-1-carboxylic acid tert-butyl ester (50.0 mg, 24.4%): HPLC-MS (ESI): Calcd for C$_{23}$H$_{24}$Cl$_2$N$_2$O$_5$S [M+H]$^+$ 511, found: 511.

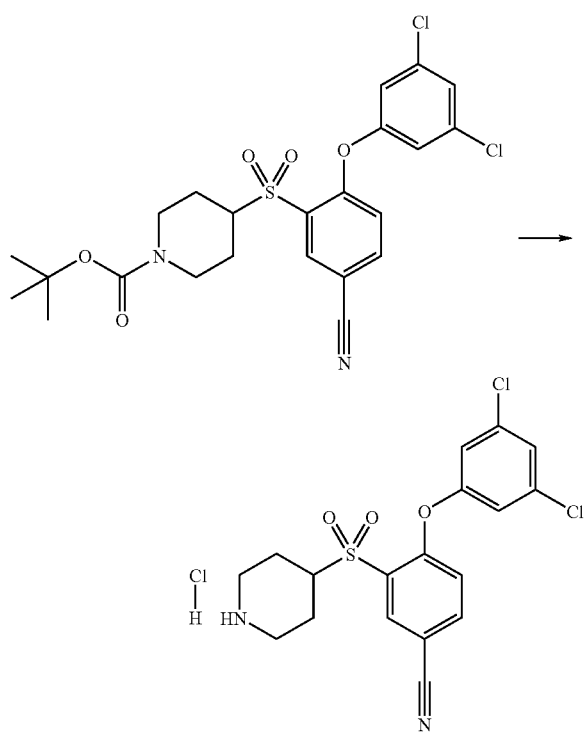

(6) To a solution in 4-[5-cyano-2-(3,5-dichloro-phenoxy)-benzenesulfonyl]-piperidine-1-carboxylic acid tert-butyl ester (30 mg, 0.06 mmol) in CH$_2$Cl$_2$ (1 ml) was added 4N HCl (in dioxane, 0.6 ml) and the mixture was stirred at room temperature for 1.5 hours. The produced white precipitate was collected by filtration and dried in vacuo to give 4-(3,5-Dichloro-phenoxy)-3-(piperidine-4-sulfonyl)-benzonitrile; hydro-chloride (23 mg, 87.6%).

$^1$H NMR(300 MHz, DMSO-d$_6$): 1.72-1.77 (2H, ddm, J=13.4 Hz, J=3.78 Hz), 2.03-2.09 (2H, ddm, J=13.4 Hz, J=3.78 Hz), 3.09 (2H, br, S), 3.18(2H, br, S), 4.94 (1H, q, J=3.78 Hz), 7.54(1H, d, J=9.03 Hz), 7.96 (2H, s), 8.07 (1H, s), 8.76 (1H, s), 8.46 (1H, s), 8.83 (1H, br, S), 9.14 (1H, br, S); HPLC-MS (ESI): Calcd for C$_{18}$H$_{17}$Cl$_3$N$_2$O$_3$S [M+H]$^+$ 411, found: 411.

Molecular weight: 447.77
Melting point: 220-226° C. (decomp.)
Activity grade CCR3: C
Activity grade IC$_{50}$: C Example 3-1

N-(1-aza-bicyclo[2.2.2]oct-3-yl)-2-(3,5-dichlorophenylsulfanyl)-5-nitro-benzene sulfonamide

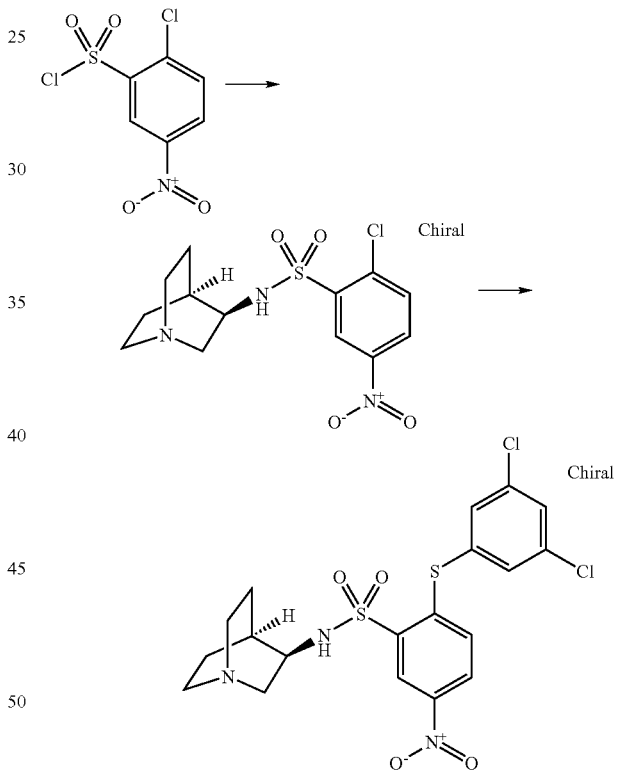

(1) To a suspension of 1-aza-bicyclo[2.2.2]oct-3-ylamine dihydrogen chloride (44.9 mg, 0.205 mmol) in THF was added NaH (60%, 41.0 mg, 1.03 mmol) portion wise, and the mixture was stirred for 30 minutes. The stirred mixture was then added to a solution of 2-chloro-5-nitro-benzenesulfonyl chloride (52.5 mg, 0.205 mmol) in THF drop wise at 0° C. The resulting mixture was stirred at 0° C. for 2 hours.

(2) After removing an ice bath, NaH (60%, 9.80 mg, 0.246 mmol) was added to the mixture followed by the addition of 3,5-dichloro-benzenethiol (44.0 mg, 0.246 mmol). The mixture was stirred at room temperature for 2 hours, and concentrated in vacuo. The residue was diluted by EtOAc and washed with water, 1N NaOH, and brine. The organic layer was dried over MgSO$_4$, and concentrated in vacuo to give crude product. The crude compound was further purified by preparative TLC to give N-(1-aza-bicyclo[2.2.2] oct-3-yl)-2-(3,5-dichloro-phenyl-sulfanyl)-5-nitro-benzenesulfonamide (41.3 mg, 41.3%) as a white powder:

$^1$H NMR (300 MHz, CDCl$_3$) δ 1.48-1.59 (1H, m), 1.61-1.73 (1H, m), 1.75-1.83 (2H, m), 2.54-2.61 (1H, m), 2.64-2.82 (2H, m), 2.85-2.90 (2H, t, J=7.5 Hz), 3.19-3.27 (1H, dd, J=9.4, 14.1 Hz), 3.42-3.46 (1H, m), 7.13-7.16 (1H, d, J=8.9 Hz), 7.39-7.40 (2H, d, J=1.9 Hz), 7.52-7.53 (1H, t, J=1.9 Hz), 8.18-8.22 (1H, dd, J=2.6, 8.9 Hz), 8.87-8.88 (1H, d, J=2.5 Hz); HPLC-MS (ESI): Calcd for C$_{19}$H$_{19}$Cl$_2$N$_3$O$_4$S$_2$[M+H]$^+$ 488, found: 488.

Molecular weight: 488.41
Melting point: 256° C.

The invention claimed is:

1. A compound of the formula (I), its tautomeric or stereoisomeric form, or a physiologically acceptable salt thereof:

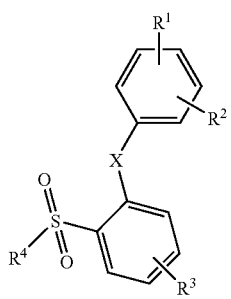

(I)

wherein
X represents O or S;
R$^1$ represents hydrogen, halogen, hydroxy, nitro, cyano, C$_{1-6}$ alkoxy carbonyl, amino, C$_{1-6}$ alkylamino, di(C$_{1-6}$ alkyl)amino, C$_{1-6}$ alkanoyl, phenyl, C$_{1-6}$ alkyl optionally substituted by mono-, di- or tri-halogen, or C$_{1-6}$ alkoxy optionally substituted by mono-, di- or tri-halogen;
R$^2$ represents hydrogen, halogen, hydroxy, nitro, cyano, C$_{1-6}$ alkoxy carbonyl, amino, C$_{1-6}$ alkylamino, di(C$_{1-6}$ alkyl)amino, C$_{1-6}$ alkanoyl, phenyl, C$_{1-6}$ alkyl optionally substituted by mono-, di- or tri-halogen, or C$_{1-6}$ alkoxy optionally substituted by mono-, di- or tri-halogen;
R$^3$ represents hydrogen, halogen, hydroxy, nitro, cyano, amino, carboxy, tetrazolyl, C$_{1-6}$ alkoxy, C$_{1-6}$ alkoxycarbonyl, C$_{1-6}$ alkanoyl, C$_{1-6}$ alkanoylamino, C$_{1-6}$ alkyl optionally substituted by mono-, di- or tri-halogen or hydroxy;
R$^4$ represents

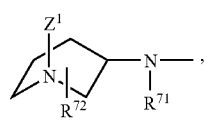

wherein:
R$^{71}$ represents hydrogen, or C$_{1-6}$ alkyl optionally substituted by amino, hydroxy, carboxy, pyrrolidinyl or piperidinyl, wherein said pyrrolidinyl and piperidinyl are optionally substituted by mono- or di-oxo;
R$^{72}$ represents hydrogen, carboxy, C$_{1-6}$ alkanoyl, amino, (C$_{1-6}$alkyl)amino, di(C$_{1-6}$alkyl)amino, N—(C$_{1-6}$alkyl) amino carbonyl, C$_{1-6}$ alkyl optionally substituted by hydroxy, carboxy, or mono-, di- or tri-halogen, C$_{1-6}$ alkoxy optionally substituted by mono-, di- or tri-halogen, pyrrolidinyl or piperidinyl, wherein said pyrrolidinyl and piperidinyl are optionally substituted by mono- or di-oxo; and Z$^1$ represents —[CH$_2$]$_p$—, wherein p is 2.

2. The compound of the formula (I), its tautomeric or stereoisomeric form, or a physiologically acceptable salt thereof as claimed in claim 1,
wherein R$^4$ represents

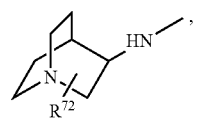

wherein:
R$^{72}$ represents hydrogen, carboxy, C$_{1-6}$ alkanoyl, amino, (C$_{1-6}$alkyl)amino, di(C$_{1-6}$alkyl)amino, N—(C$_{1-6}$alkyl) amino carbonyl, C$_{1-6}$ alkyl optionally substituted by hydroxy, carboxy, or mono-, di- or tri-halogen, C$_{1-6}$ alkoxy option substituted by mono-, di- or tri-halogen, pyrrolidinyl or piperidinyl wherein said pyrrolidinyl and piperidinyl are optionally substituted by mono- or di-oxo.

3. The compound of claim 1, wherein the derivative is of the formula (I-b), its tautomeric or stereoisomeric form, or a physiologically acceptable salt thereof:

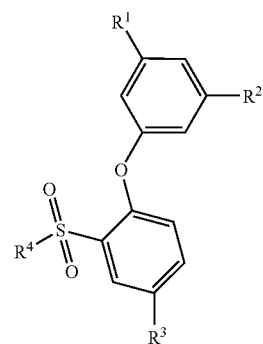

(I-b)

wherein:
R$^1$ represents fluoro, chloro, bromo, iodo, or nitro;
R$^2$ represents fluoro, chloro, bromo, iodo, or nitro;
R$^3$ represents acetyl, cyano, or tetrazolyl;
R$^4$ represents

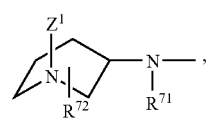

wherein:
R$^{71}$ represents hydrogen, or C$_{1-6}$ alkyl optionally substituted by amino, hydroxy, carboxy, pyrrolidinyl or piperidinyl, wherein said pyrrolidinyl and piperidinyl are optionally substituted by mono- or di-oxo;

$R^{72}$ represents hydrogen, carboxy, $C_{1-6}$ alkanoyl, amino, $(C_{1-6}$alkyl)amino, di($C_{1-6}$alkyl)amino, N—($C_{1-6}$alkyl) amino carbonyl, $C_{1-6}$ alkyl optionally substituted by hydroxy, carboxy, or mono-, di- or tri-halogen, $C_{1-6}$ alkoxy optionally substituted by mono-, di- or tri-halogen, pyrrolidinyl or piperidinyl, wherein said pyrrolidinyl and piperidinyl are optionally substituted by mono- or di-oxo; and $Z^1$ represents —[$CH_2$]$_p$—, wherein p is 2.

4. The compound of claim 3, its tautomeric or stereoisomeric form, or a physiologically acceptable salt thereof, wherein:

$R^1$ represents fluoro, chloro or bromo;
$R^2$ represents fluoro, chloro or bromo;
$R^3$ represents cyano;
$R^4$ represents

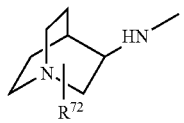

wherein:
$R^{72}$ represents hydrogen, carboxy, $C_{1-6}$ alkanoyl, amino, $(C_{1-6}$alkyl)amino, di($C_{1-6}$alkyl)amino, N—($C_{1-6}$alkyl) amino carbonyl, $C_{1-6}$ alkyl optionally substituted by hydroxy, carboxy, or mono-, di- or tri-halogen, $C_{1-6}$ alkoxy optionally substituted by mono-, di- or tri-halogen, pyrrolidinyl or piperidinyl wherein said pyrrolidinyl and piperidinyl are optionally substituted by mono- or di-oxo.

5. A compound of claim 1, its tautomeric or stereoisomeric form, or a physiologically acceptable salt thereof, wherein said compound is selected from the group consisting of:

(R)-N-(1-Aza-bicyclo[2.2.2]oct-3-yl)-5-cyano-2-(3,5-dichloro-phenoxy)-benzenesulfonamide;

(S)-N-(1-Aza-bicyclo[2.2.2]oct-3-yl)-5-cyano-2-(3,5-dichloro-phenoxy)-benzenesulfonamide;

N-(1-aza-bicyclo[2.2.2]oct-3-yl)-2-(3,5-dichloro-phenyl-sulfanyl)-5-nitro-benzenesulfonamide; and (R)-5-cyano-2-(3,5-dichlorophenoxy)-N-(2-(2,5-dioxopyrrolidin-1-yl)ethyl)-N-(1-aza-bicyclo[2.2.2]oct-3-yl)benzenesulfonamide.

6. A pharmaceutical composition comprising a compound of claim 1, its tautomeric or stereoisomeric form, or a physiologically acceptable salt thereof as an active ingredient, and one or more pharmaceutically acceptable excipients.

7. A method of treating asthma, allergic rhinitis or lung granuloma, comprising administering a compound of claim 1 or its tautomeric or stereoisomeric form, or a physiologically acceptable salt thereof.

8. The method of claim 7, wherein said compound, its tautomeric or stereoisomeric form, or a physiologically acceptable salt thereof is formulated with one or more pharmaceutically acceptable excipients.

9. The pharmaceutical composition of claim 6 wherein the excipient is an inert substance selected from the group consisting of a carrier, a diluent, a flavoring agent, a sweetener, a lubricant, a solubilizer, a suspending agent, a binder, a tablet disintegrating agent and an encapsuling agent.

10. The method of claim 8 wherein the excipient is an inert substance selected from the group consisting of a carrier, a diluent, a flavoring agent, a sweetener, a lubricant, a solubilizer, a suspending agent, a binder, a tablet disintegrating agent and an encapsuling agent.

* * * * *

UNITED STATES PATENT AND TRADEMARK OFFICE
CERTIFICATE OF CORRECTION

PATENT NO.      : 7,674,797 B2
APPLICATION NO. : 10/550482
DATED           : March 9, 2010
INVENTOR(S)     : Li et al.

It is certified that error appears in the above-identified patent and that said Letters Patent is hereby corrected as shown below:

Column 69, lines 55-60, the chemical structure

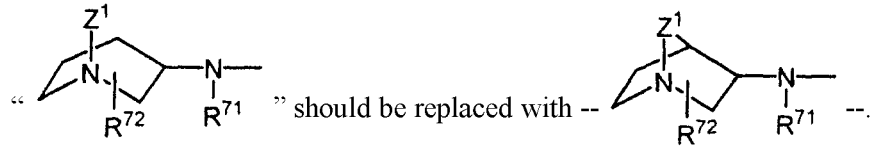

Column 70, lines 55-60, the chemical structure

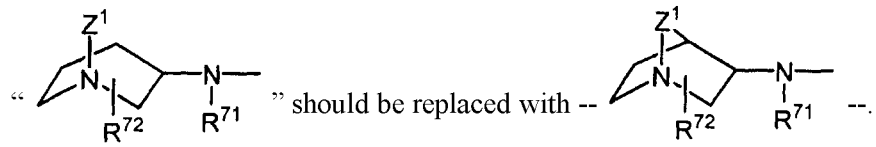

Signed and Sealed this

Fifteenth Day of June, 2010

David J. Kappos
*Director of the United States Patent and Trademark Office*